US012624066B2

(12) United States Patent
Slilaty

(10) Patent No.: US 12,624,066 B2
(45) Date of Patent: May 12, 2026

(54) INHIBITORS OF CORONAVIRUS PROTEASE

(71) Applicant: SUNSHINE BIOPHARMA INC., Centennial, CO (US)

(72) Inventor: Steve N. Slilaty, Laval (CA)

(73) Assignee: Sunshine Biopharma Inc., Centennial, CO (US)

( * ) Notice: Subject to any disclaimer, the term of this patent is extended or adjusted under 35 U.S.C. 154(b) by 706 days.

(21) Appl. No.: 17/926,892

(22) PCT Filed: Apr. 30, 2021

(86) PCT No.: PCT/IB2021/053645
§ 371 (c)(1),
(2) Date: Nov. 21, 2022

(87) PCT Pub. No.: WO2021/234483
PCT Pub. Date: Nov. 25, 2021

(65) Prior Publication Data

US 2023/0234986 A1 Jul. 27, 2023

Related U.S. Application Data

(60) Provisional application No. 63/028,871, filed on May 22, 2020.

(51) Int. Cl.
*C07K 7/06* (2006.01)
*A61P 31/14* (2006.01)

(52) U.S. Cl.
CPC ................ *C07K 7/06* (2013.01); *A61P 31/14* (2018.01)

(58) Field of Classification Search
None
See application file for complete search history.

(56) References Cited

U.S. PATENT DOCUMENTS

| | | | |
|---|---|---|---|
| 5,175,254 | A | 12/1992 | Calas et al. |
| 6,506,731 | B1 | 1/2003 | Sandberg et al. |

OTHER PUBLICATIONS

Stein et al (Biochemistry 34:12616-12623, 1995) (Year: 1995).*
Pubchem SID 29979853 deposited on Dec. 4, 2007 (Dec. 4, 2007) pp. 1-5. p. 2.
Rut et al. 'Activity Profiling of SARS-CoV-2-PLpro-Protease-Provides Structural Framework for Anti-COVID-19 Drug Design', bioRxiv, Apr. 29, 2020 (Apr. 29, 2020) pp. 1-17. Entire Document.
International Search Report of PCT/IB2021/053645; Aug. 26, 2021; Rodriquez Kari.

* cited by examiner

*Primary Examiner* — Craig D Ricci
(74) *Attorney, Agent, or Firm* — DECODE LEGAL INC.; Mathieu Miron

(57) ABSTRACT

The present document describes compounds that are inhibitors of coronavirus proteases, and more particularly to compounds that are inhibitors of SARS-CoV-2 viral proteases. Also, the present document describes methods and uses of the compounds for the treatment or prevention of viral infection, such as SARS-CoV-2 infections, in a subject in need of treatment.

2 Claims, No Drawings

INHIBITORS OF CORONAVIRUS PROTEASE

CROSS-REFERENCE TO RELATED APPLICATIONS

This application is a U.S. National Phase application under 35 U.S.C. § 371 of PCT/IB2021/053645, filed Apr. 30, 2021, which claims priority from and the benefit of U.S. Provisional Patent Application No. 63/028,871 filed on May 22, 2020, the specifications of which are hereby incorporated by reference in their entireties.

BACKGROUND

(A) Field

The subject matter disclosed generally relates to compounds that are inhibitors of coronavirus proteases, and more particularly to compounds that are inhibitors of SARS-CoV-2 viral proteases.

(b) Related Prior Art

Severe Acute Respiratory Syndrome-Coronavirus-2 (SARS-CoV-2) is the causative agent of COVID-19, the pandemic that has claimed the lives of millions of people worldwide since it first appeared in the fall of 2019. SARS-CoV-2 is a Betacoronaviruses, one of four genera of Coronaviruses belonging to the family, Coronaviridae. The three genera are Alpha, Gamma and Delta Coronavirus. The Gamma and Delta Coronaviruses do not infect humans while the Alpha genus is responsible for about 30% of the common cold.

The Betacoronavirus genus is comprised of: (i) SARS-CoV which appeared in 2002 and had an associated mortality rate of 10 to 15 percent, (ii) MERS-CoV which came on the scene in 2015 wielding a case-fatality rate of 34 to 37 percent, and (iii) SARS-CoV-2, the causative agent of the 2020 pandemic with a mortality rate of 3 to 5 percent.

In addition to the main protease (Mpro), which is shared among coronaviruses, Betacoronaviruses have a second virus-encoded protease called papain-like protease (PLpro). These two proteases are responsible for cleaving the initial expression products of the viral genome (polyproteins 1a and 1ab) at 15 different sites to produce 16 different mature virus proteins essential for viral replication. While Mpro cleaves the viral polyproteins 1a and 1ab at 12 different locations, PLpro cleaves polyprotein 1a at only 3 sites. PLpro however is also involved in cleaving certain host proteins (various ubiquitinated proteins and ISG15) resulting in suppression of the host innate immune response thereby allowing virus replication to proceed unchecked. It is believed that enhanced pathogenicity is related to this additional protease activity that Betacoronaviruses possess.

Consequently, in view of the global pandemic of SARS-CoV-2, the Mpro and PLpro of this novel coronavirus may be critical drug targets, suggesting that inhibitors of these enzymes may be beneficial in its inactivation for prevention or treatment of the COVID-19 disease.

SUMMARY

According to an embodiment, there is provided a compound of formula I, or a pharmaceutically acceptable salts thereof, and stereoisomers thereof:

(I)

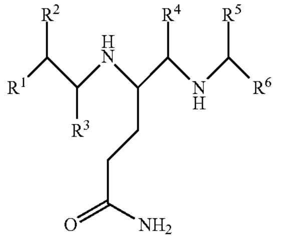

wherein

- $R^1$ is $NH_2$ or $NHR^{1'}$ where $R^{1'}$ is a suitable protecting group for an amine group;
- $R^2$ is selected from the group consisting of

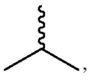, 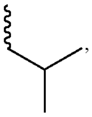, 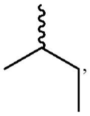, and 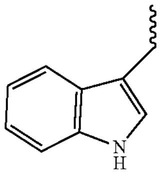;

- $R^3$ is =O, —OH or absent;
- $R^4$ is =O, —OH, —SH, or absent;
- $R^5$ is absent or is selected from the group consisting of —$CH_3$, —$CH_2$—OH, and

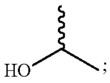;

and

- $R^6$ is —C(O)OH or —C(O)$OR^{6'}$, where $R^{6'}$ is a or a suitable protecting group for a hydroxyl group, wherein 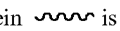 is a point of attachment with the $R^1$, $R^2$, $R^3$, $R^4$, $R^5$ or $R^6$.

The compound of formula I may be a compound of formula Ia (Ia)

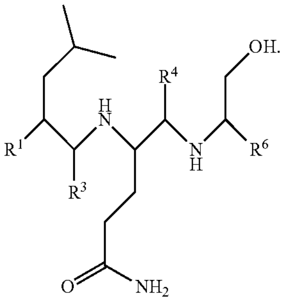

The compound of formula I may be

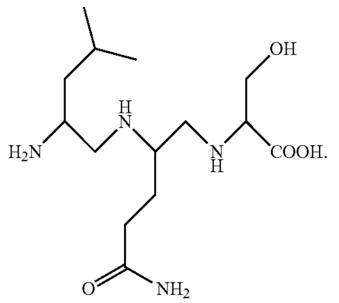 [SMILES: CC(C)CC(N)CNC(CCC(N)=O)CNC(CO)C(=O)O]

The $R^3$ and $R^4$ may be absent.

The $R^3$ may be absent and $R^4$ may be —SH.

The compound of formula I may be

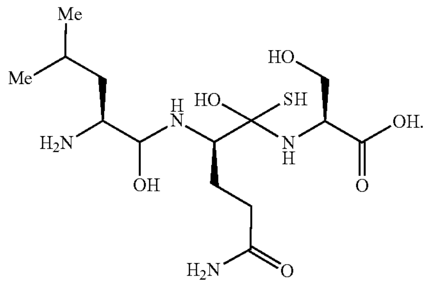 [SMILES: CC(C)C[C@H](N)C(O)N[C@H](CCC(N)=O)C(O)(S)N[C@@H](CO)C(=O)O]

The suitable protecting group for an amine group may be selected from the group consisting of carbobenzyloxy (Cbz), p-Methoxybenzyl carbonyl (MeOZ), tert-Butyloxycarbonyl (BOC), 9-Fluorenylmethyloxycarbonyl (Fmoc), acetyl (Ac), benzoyl (Bz), benzyl (Bn), p-Methoxybenzyl (PMB), 3,4-Dimethoxybenzyl (DMPM), p-Methoxyphenyl (PMP), tosyl (Ts), troc (trichloroethyl chloroformate), 4-nitrobenzene-1-sulfonyl chloride (Nosyl) and 2-Nitrophenylsulfenyl (Nps).

The suitable protecting group for a hydroxyl group may be selected from the group consisting of alkyl, acetyl (Ac), benzoyl (Bz), benzyl (Bn), p-Methoxyethoxymethyl ether (MEM), [bis-(4-methoxyphenyl)phenylmethyl] (DMT), methoxymethyl ether (MOM), methoxytrityl [(4-methoxyphenyl)diphenylmethyl] (MMT), p-Methoxybenzyl ether (PMB), methylthiomethyl ether, pivaloyl (Piv), tetrahydropyranyl (THP), tetrahydrofuran (THF), trityl (triphenylmethyl, Tr), trimethylsilyl (TMS), tertiobutyldiphenylsilyl (TBDPS), tert-butyldimethylsilyl (TBDMS), tri-iso-propylsilyloxymethyl (TOM), triisopropylsilyl (TIPS), methyl ethers, and ethoxyethyl ethers (EE).

According to another embodiment, there is provided a pharmaceutical composition comprising a compound of the present invention or a pharmaceutically acceptable salt thereof, and a pharmaceutically acceptable carrier.

According to another embodiment, there is provided a use of a compound of any one of the present invention or a pharmaceutically acceptable salt thereof for the manufacture of a medicament for treatment or prevention of a viral infection in a subject in need thereof.

According to another embodiment, there is provided a use of a compound of the present invention, or a pharmaceutically acceptable salt thereof, or the composition of the present invention, for treatment or prevention of a viral infection in a subject in need thereof.

According to another embodiment, there is provided a compound of the present invention, or a pharmaceutically acceptable salt thereof for use in the treatment or prevention of a viral infection in a subject in need thereof.

According to another embodiment, there is provided a method of treating or preventing a viral infection in a subject in need thereof comprising administering a therapeutically effective amount a compound of the present invention, or a pharmaceutically acceptable salt thereof, or the composition of the present invention, to the subject.

According to another embodiment, there is provided a compound of formula II, or a pharmaceutically acceptable salts thereof, and stereoisomers thereof:

$$X_0—X_1—X_2—X_3—X_4—X_5—X_6—X_7$$

wherein $X_0$ is

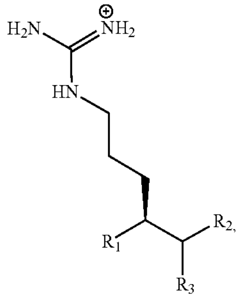
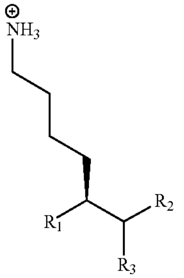

or absent, $X_1$ is

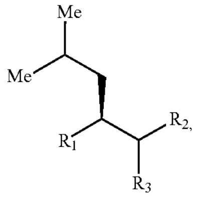
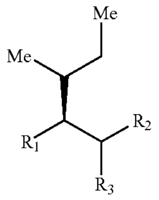

or absent, $X_2$ is

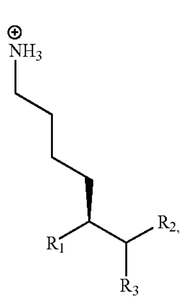
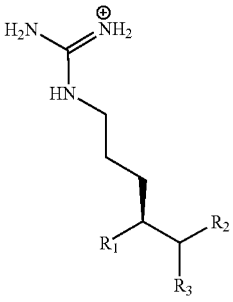

or absent, $X_3$ or $X_4$ is

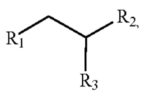

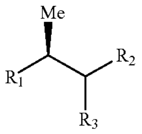

or absent, $X_5$ is

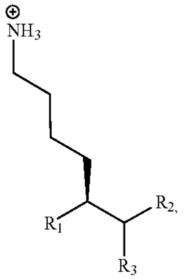

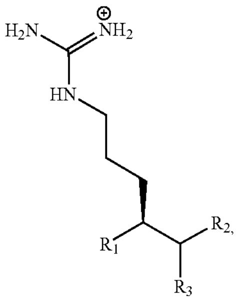

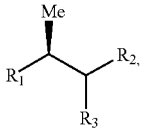

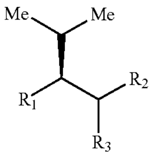

or absent, $X_6$ is

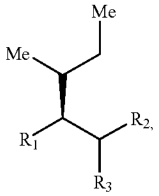

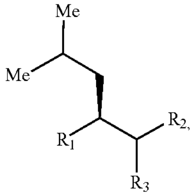

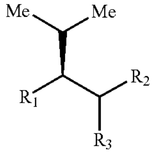

or absent, and $X_7$ is

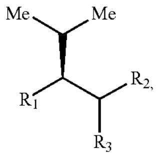

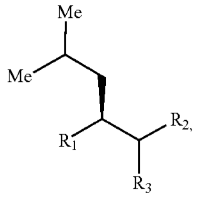

-continued

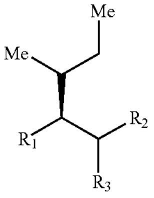

or absent, wherein said compound comprises a minimum of four of said consecutive $X_0$, $X_1$, $X_2$, $X_3$, $X_4$, $X_5$, $X_6$, and $X_7$, wherein $R^1$ is

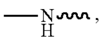

$NH_2$ or $NHR^{1'}$ where $R^{1'}$ is a suitable protecting group for an amine group, or a chromophore;

$R^2$ is 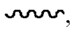, —OH or —$OR^{3'}$, where $R^{3'}$ is a or a suitable protecting group for a hydroxyl group, or a chromophore, $R^3$ is =O, —OH or absent;

wherein  is a point of attachment between said $X_1$ and $X_2$, $X_2$ and $X_3$, $X_3$ and $X_4$, $X_4$ and $X_5$, $X_5$ and $X_6$, or $X_6$ and $X_7$.

The compound of formula II may be a compound of formula IIa

IIa

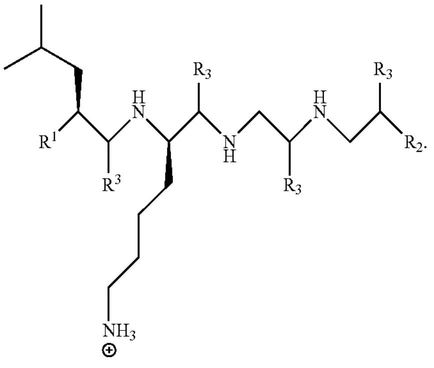

The compound of formula II may be
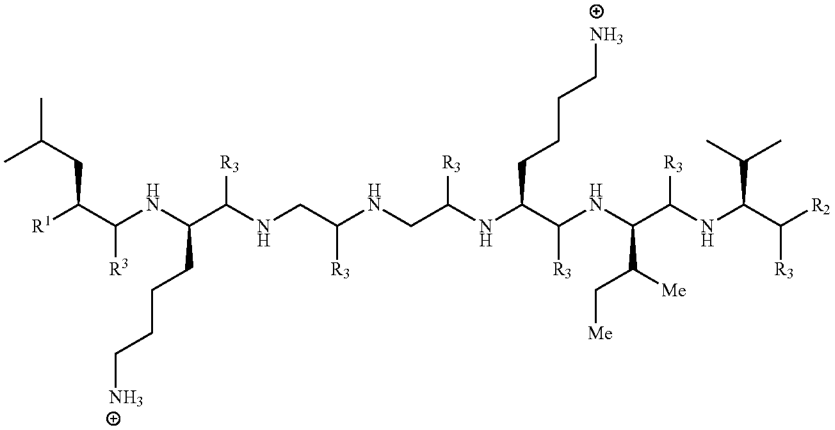
The $R_1$ is $NH_2$, $R_2$ may be —C(O)OH, and $R_3$ may be =O.
The compound of formula II may be
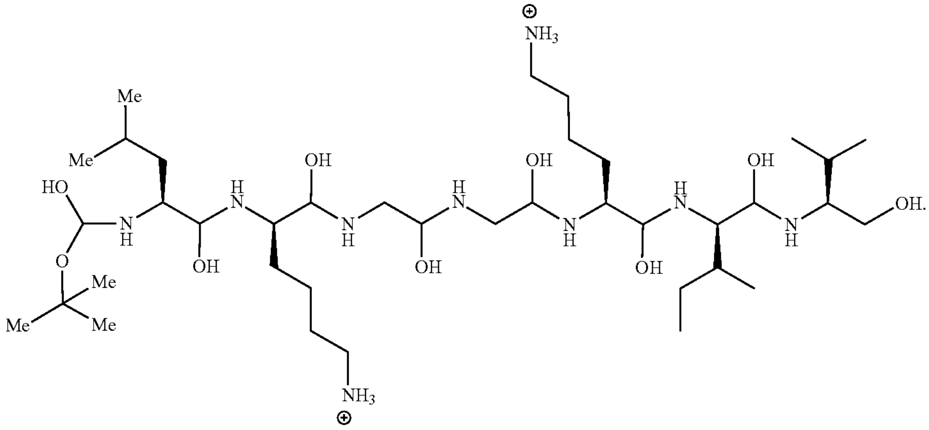 [SMILES: CCC(C)[C@@H](NC(O)[C@H](CCCC[NH3+])NC(O)CNC(O)CNC(O)[C@@H](CCCC[NH3+])NC(O)[C@H](CC(C)C)NC(O)OC(C)(C)C)C(O)N[C@H](CO)C(C)C]
The compound of formula II may be any one of the following compounds:
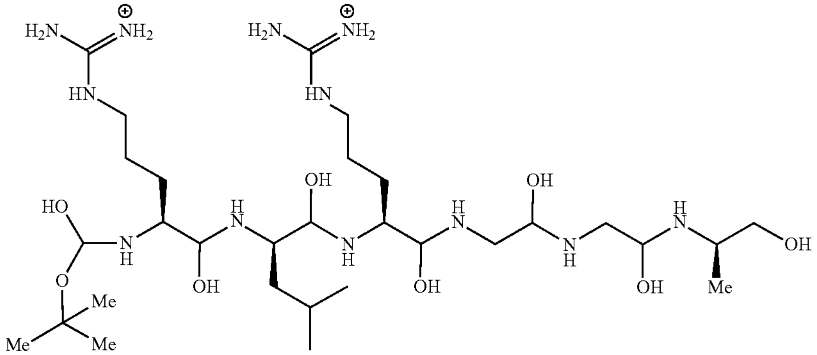
or -continued

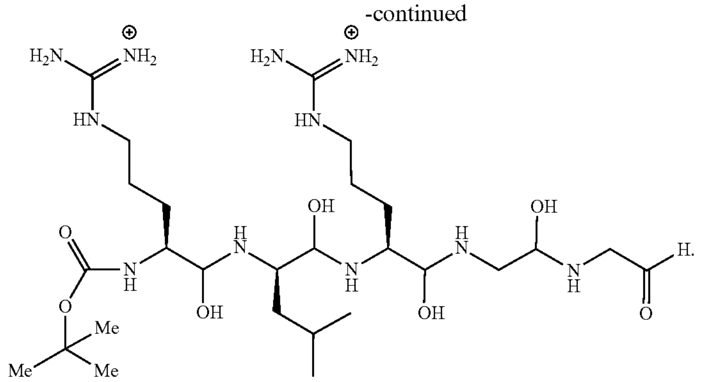

The compound of formula II may be the following compound:

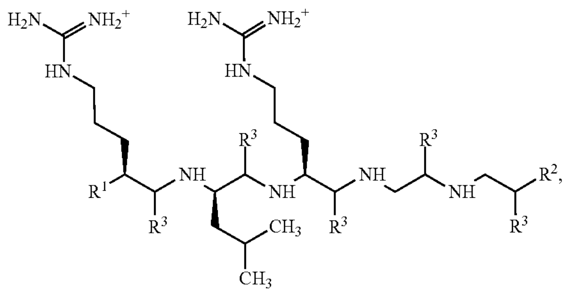

wherein $R^1$ is —$NH_2$, $R^2$ is —OH; and $R^3$ is absent.

The compound of formula II may be the following compound:

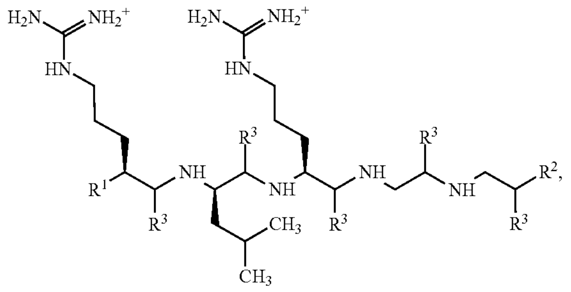

wherein $R^1$ is —$NH_2$, $R^2$ is —OH; and $R^3$ is —OH.

The compound of formula II may be the following compound:

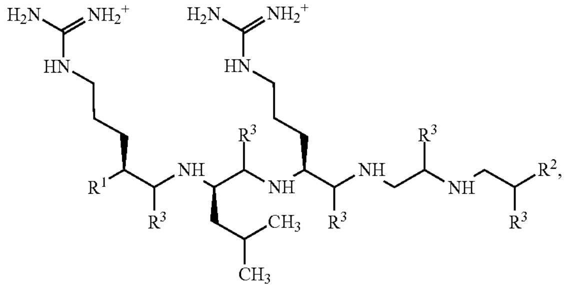

wherein $R^1$ is —$NH_2$, $R^2$ is —OH; and $R^3$ is =O.

The compound of formula II may be the following compound:

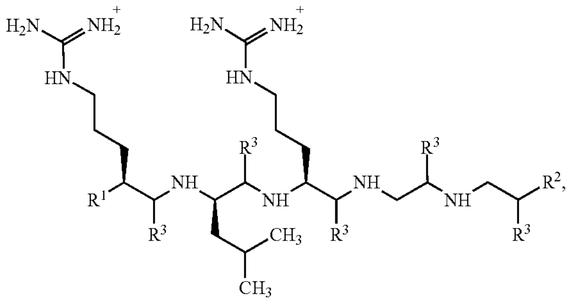

wherein $R^1$ is —$NH_2$;

$R^2$ is —$OR^{3'}$, where $R^{3'}$ is 7-Amino-4-methylcoumarin (AMC); and $R^3$ is absent.

The compound of formula II may be the following compound:

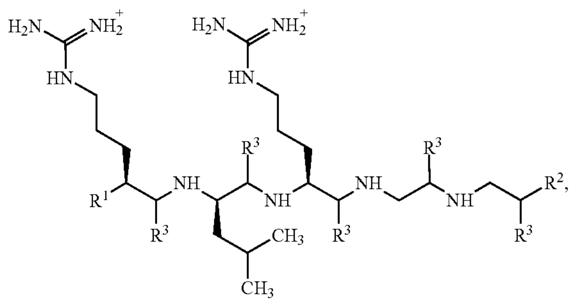

wherein $R^1$ is —$NH_2$;

$R^2$ is —$OR^{3'}$, where $R^{3'}$ is 7-Amino-4-methylcoumarin (AMC); and $R^3$ is —OH.

The compound of formula II may be the following compound:

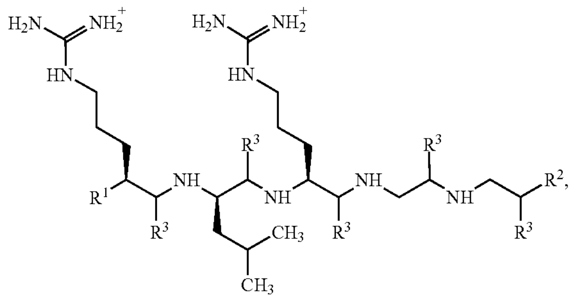

wherein $R^1$ is —$NHR^{1'}$, where $R^{1'}$ is carbobenzyloxy (Cbz);

$R^2$ is —$OR^{3'}$, where $R^{3'}$ is 7-Amino-4-methylcoumarin (AMC); and $R^3$ is absent.

The compound of formula II may be the following compound:

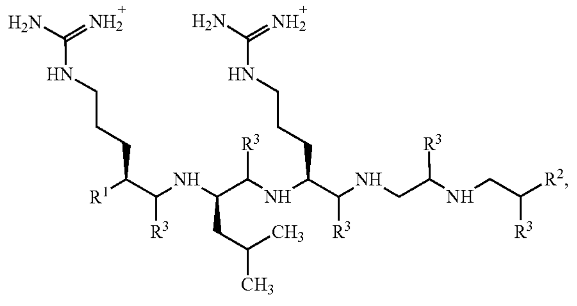

wherein $R^1$ is —$NHR^{1'}$, where $R^{1'}$ is carbobenzyloxy (Cbz);

$R^2$ is —$OR^{3'}$, where $R^{3'}$ is 7-Amino-4-methylcoumarin (AMC); and $R^3$ is —OH.

The compound of formula II may be the following compound:

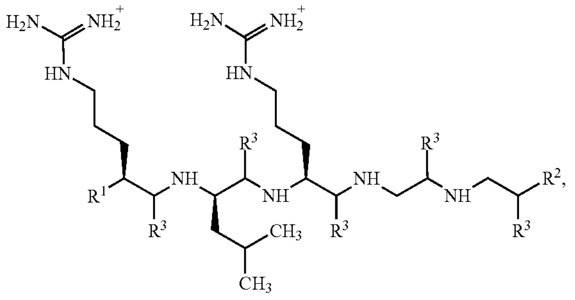

wherein $R^1$ is —$NHR^{1'}$, where $R^{1'}$ is carbobenzyloxy (Cbz);

$R^2$ is —$OR^{3'}$, where $R^{3'}$ is carbobenzyloxy (Cbz); and $R^3$ is absent.

The compound of formula II may be the following compound:

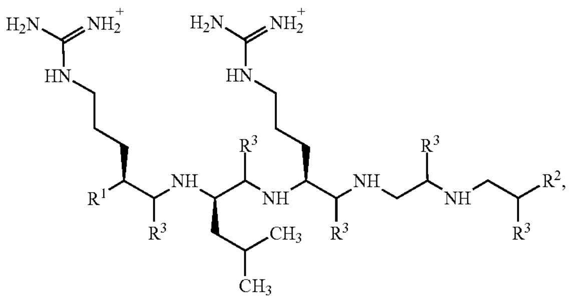

wherein $R^1$ is —$NHR^{1'}$, where $R^{1'}$ is carbobenzyloxy (Cbz);

$R^2$ is —$OR^{3'}$, where $R^{3'}$ is carbobenzyloxy (Cbz); and $R^3$ is —OH.

The compound of formula II may be the following compound:
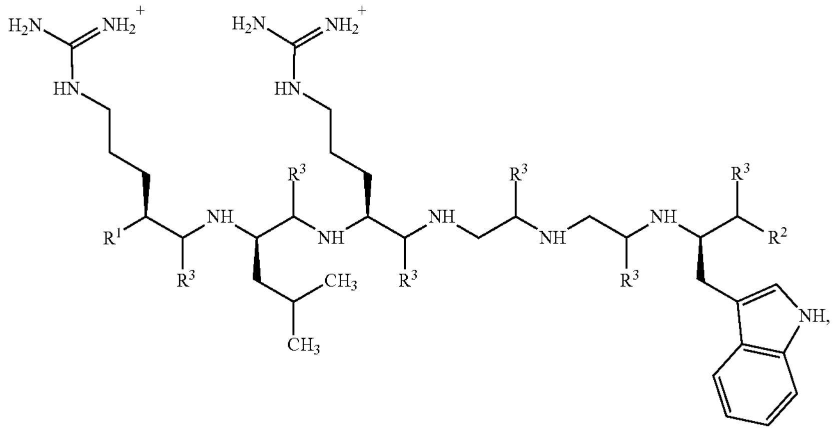
wherein
$R^1$ is —$NHR^{1'}$, where $R^{1'}$ is carbobenzyloxy (Cbz);
$R^2$ is —OH; and
$R^3$ is absent.
The compound of formula II may be the following compound:
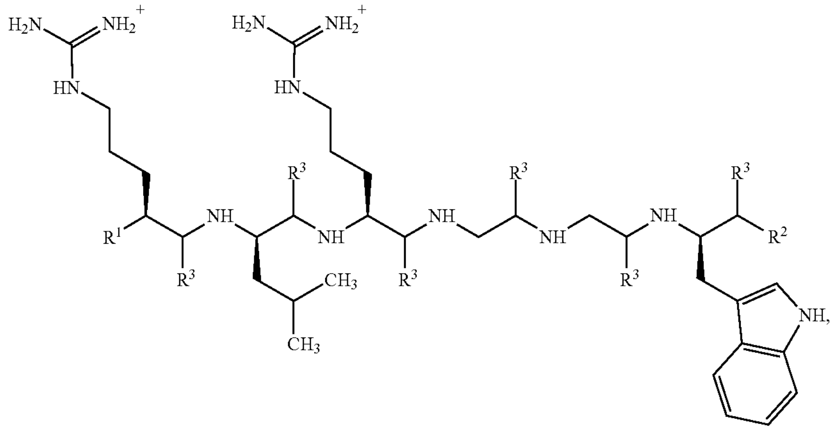
wherein
$R^1$ is —$NHR^{1'}$, where $R^{1'}$ is carbobenzyloxy (Cbz);
$R^2$ is —OH; and
$R^3$ is —OH.
The compound of formula II may be the following compound:
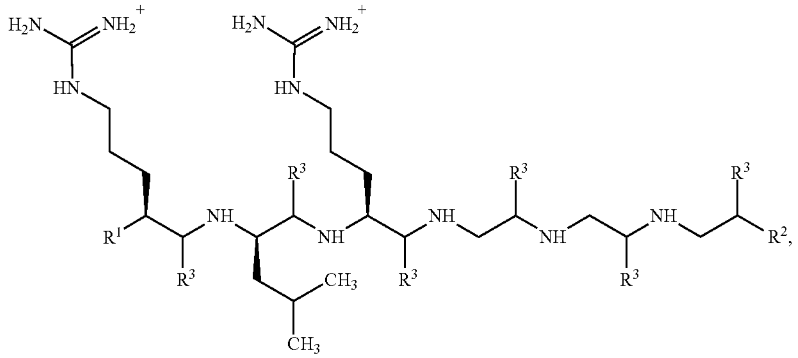

wherein $R^1$ is —$NHR^{1'}$, where $R^{1'}$ is carbobenzyloxy (Cbz);

$R^2$ is —$OR^{3'}$, where $R^{3'}$ is 7-Amino-4-methylcoumarin (AMC); and $R^3$ is absent.

The compound of formula II may be the following compound:

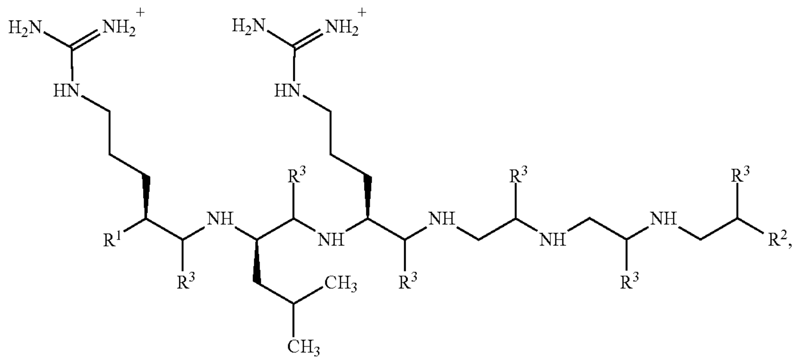

wherein $R^1$ is —$NHR^{1'}$, where $R^{1'}$ is carbobenzyloxy (Cbz);

$R^2$ is —$OR^{3'}$, where $R^{3'}$ is 7-Amino-4-methylcoumarin (AMC); and $R^3$ is —OH.

The compound of formula II may be the following compound:

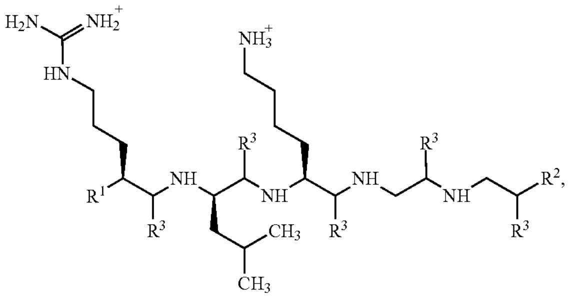

wherein $R^1$ is —$NH_2$;

$R^2$ is —OH; and $R^3$ is =O.

The compound of formula II may be the following compound:

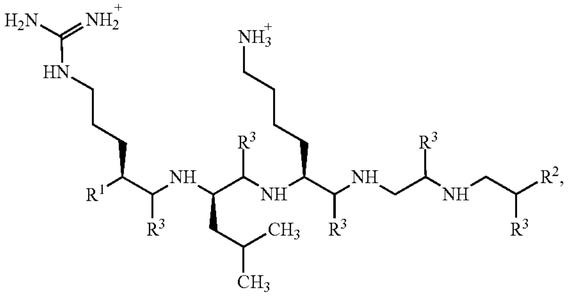

wherein $R^1$ is —$NH_2$;

$R^2$ is —OH; and $R^3$ is =O.

The compound of formula II may be the following compound:

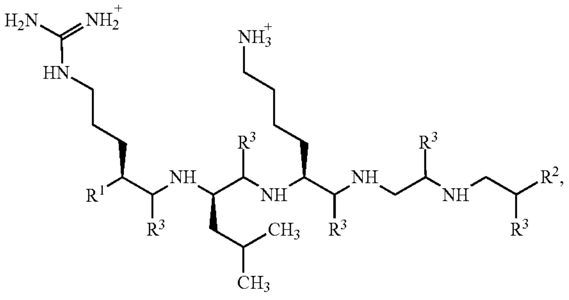

wherein $R^1$ is —$NH_2$;

$R^2$ is —OH; and $R^3$ is —OH.

The suitable protecting group for an amine group may be selected from the group consisting of carbobenzyloxy (Cbz), p-Methoxybenzyl carbonyl (MeOZ), tert-Butyloxycarbonyl (BOC), 9-Fluorenylmethyloxycarbonyl (Fmoc), acetyl (Ac), benzoyl (Bz), benzyl (Bn), p-Methoxybenzyl (PMB), 3,4-Dimethoxybenzyl (DMPM), p-Methoxyphenyl (PMP), tosyl (Ts), troc (trichloroethyl chloroformate), 4-nitrobenzene-1-sulfonyl chloride (Nosyl) and 2-Nitrophenylsulfenyl (Nps).

The suitable protecting group for a hydroxyl group may be selected from the group consisting of alkyl, acetyl (Ac), benzoyl (Bz), benzyl (Bn), p-Methoxyethoxymethyl ether (MEM), [bis-(4-methoxyphenyl)phenylmethyl] (DMT), methoxymethyl ether (MOM), methoxytrityl [(4-methoxyphenyl)diphenylmethyl] (MMT), p-Methoxybenzyl ether (PMB), methylthiomethyl ether, pivaloyl (Piv), tetrahydropyranyl (THP), tetrahydrofuran (THF), trityl (triphenylmethyl, Tr), trimethylsilyl (TMS), tertiobutyldiphenylsilyl (TBDPS), tert-butyldimethylsilyl (TBDMS), tri-iso-propylsilyloxymethyl (TOM), triisopropylsilyl (TIPS), methyl ethers, and ethoxyethyl ethers (EE).

The chromophore may be 7-Amino-4-methylcoumarin (AMC).

According to another embodiment, there is provided a pharmaceutical composition comprising a compound of the present invention or a pharmaceutically acceptable salt thereof, and a pharmaceutically acceptable carrier.

According to another embodiment, there is provided a use of a compound of any one of the present invention or a pharmaceutically acceptable salt thereof for the manufacture of a medicament for treatment or prevention of a viral infection in a subject in need thereof.

According to another embodiment, there is provided a use of a compound of the present invention, or a pharmaceutically acceptable salt thereof, or the composition of the present invention, for treatment or prevention of a viral infection in a subject in need thereof.

According to another embodiment, there is provided a compound of the present invention, or a pharmaceutically acceptable salt thereof for use in the treatment or prevention of a viral infection in a subject in need thereof.

According to another embodiment, there is provided a method of treating or preventing a viral infection in a subject in need thereof comprising administering a therapeutically effective amount a compound of the present invention, or a pharmaceutically acceptable salt thereof, or the composition of the present invention, to the subject.

In the use of the present invention, the compound for use of the present invention, or the method of the present invention, wherein the viral infection is a SARS-CoV-2 infection.

Definitions

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from C3-10, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$-), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, 2-oxopiperidin-1-yl, 2-oxopyrrolidin-1-yl, 2-oxoazetidin-1-yl, 1,2,4-oxadiazin-5(6H)-one-3-yl, and the like.

"Heteroaryl" means an aromatic or partially aromatic heterocycle that contains at least one ring heteroatom selected from O, S and N. Heteroaryls thus include heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION

In embodiments there is disclosed a compound of formula I, or a pharmaceutically acceptable salts thereof, and stereoisomers thereof, which are inhibitors of coronavirus main protease (Mpro). Particularly, the compounds of formula (I) are believed to be inhibitors of betacoronavirus main protease (Mpro):

(I)

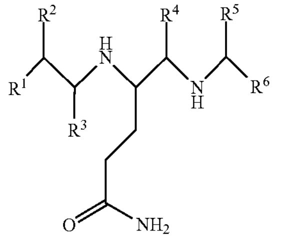

wherein $R^1$ is $NH_2$ or $NHR^{1'}$ where $R^{1'}$ is a suitable protecting group for an amine group;

$R^2$ is selected from the group consisting of

, 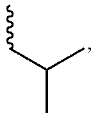, 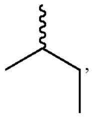, and 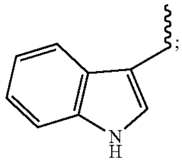;

$R^3$ is =O or absent;

$R^4$ is =O, —SH, or absent;

$R^5$ is absent or is selected from the group consisting of —$CH_3$, —$CH_2$—OH, and

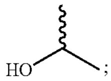;

and $R^6$ is —C(O)OH or —C(O)$OR^{6'}$, where $R^{6'}$ is a or a suitable protecting group for a hydroxyl group, wherein  is a point of attachment with the $R^1$, $R^2$, $R^3$, $R^4$, $R^5$ or $R^6$.

According to embodiments, the $R^2$ group reflects hydrophobic amino acid side chains, such as valine (Val, V), leucine (Leu, L), isoleucine (Ile, I), and also include the tryptophan (Trp, W) side chain.

According to embodiments, the $R^5$ group reflects small amino acid side chains, such as glycine (Gly, G), alanine (Ala, A) and nucleophilic small amino acid side chains such as serine (Ser, S) and threonine (Thr, T).

According to embodiments, the $R^4$ group may be an —SH group, so as to provide a reactive —SH group that may react with a viral protease.

According to another embodiment, the compound of formula I may be a compound of formula Ia Ia

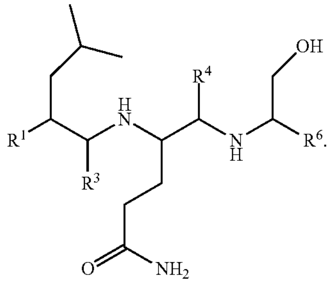

In the compound of formula Ia, the $R^2$ group reflects the amino acid side chain of leucine (Leu, L) and the $R^5$ group reflects the amino acid side chain of serine (Ser, S). The $R^1$, $R^3$, $R^4$, and $R^6$ are as defined above.

According to another embodiment, the compound of formula I is

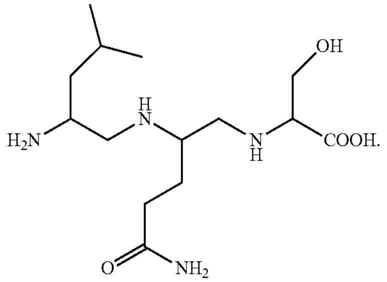 [SMILES: CC(C)CC(N)CNC(CCC(N)=O)CNC(CO)C(=O)O]

According to another embodiment, the $R^3$ and $R^4$ are absent.

According to another embodiment, the $R^3$ is absent and $R^4$ is —SH.

According to embodiments, in the compounds of the present invention, the suitable protecting group for an amine group are selected from the group consisting of carbobenzyloxy (Cbz), p-Methoxybenzyl carbonyl (MeOZ), tert-Butyloxycarbonyl (BOC), 9-Fluorenylmethyloxycarbonyl (Fmoc), acetyl (Ac), benzoyl (Bz), benzyl (Bn), p-Methoxybenzyl (PMB), 3,4-Dimethoxybenzyl (DMPM), p-Methoxyphenyl (PMP), tosyl (Ts), troc (trichloroethyl chloroformate), 4-nitrobenzene-1-sulfonyl chloride (Nosyl) and 2-Nitrophenylsulfenyl (Nps).

According to embodiments, in the compounds of the present invention, the suitable protecting group for a hydroxyl group are selected from the group consisting of alkyl, acetyl (Ac), benzoyl (Bz), benzyl (Bn), β-Methoxyethoxymethyl ether (MEM), [bis-(4-methoxyphenyl)phenylmethyl] (DMT), methoxymethyl ether (MOM), methoxytrityl [(4-methoxyphenyl)diphenylmethyl] (MMT), p-Methoxybenzyl ether (PMB), methylthiomethyl ether, pivaloyl (Piv), tetrahydropyranyl (THP), tetrahydrofuran (THF), sylil ethers such as trialkylsilyl, tertiobutyldiphenylsilyl (TBDPS), trityl (triphenylmethyl, Tr), trimethylsilyl (TMS), tert-butyldimethylsilyl (TBDMS), tri-iso-propylsilyloxymethyl (TOM), triisopropylsilyl (TIPS), methyl ethers, and ethoxyethyl ethers (EE).

The invention includes the compounds as shown, and also includes (where possible) individual diastereomers, enantiomers, and epimers of the compounds, and mixtures of diastereomers and/or enantiomers thereof including racemic mixtures. Although the specific stereochemistries disclosed herein are preferred, other stereoisomers, including diastereomers, enantiomers, epimers, and mixtures of these may also be useful in activating viral proteases. Inactive or less active diastereoisomers and enantiomers are useful for scientific studies relating to the enzyme target and the mechanism of activation.

In embodiments there is disclosed a compound of formula II, or a pharmaceutically acceptable salts thereof, and stereoisomers thereof, which are inhibitors of coronavirus papain-like protease (PLpro). Particularly, the compounds of formula II are believed to be inhibitors of betacoronavirus papain-like protease (PLpro):

$$X_0—X_1—X_2—X_3—X_4—X_5—X_6—X_7$$

wherein $X_0$ is

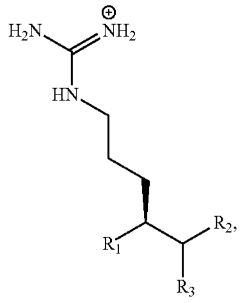

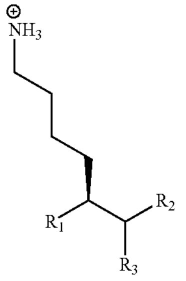

or absent, $X_1$ is

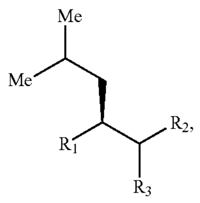

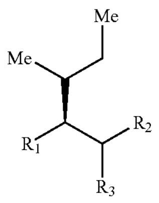

or absent, $X_2$ is

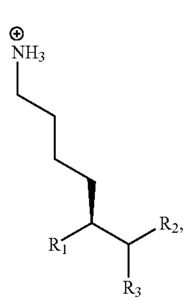

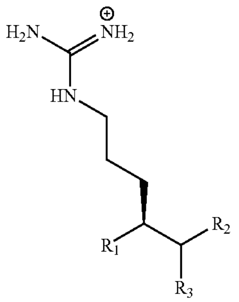

or absent, $X_3$ or $X_4$ is

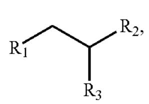

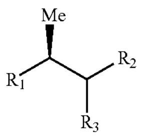

or absent, $X_5$ is

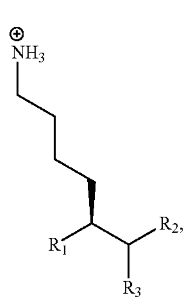

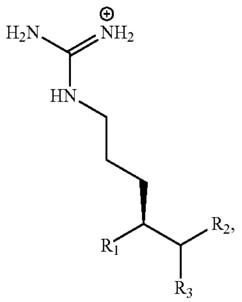

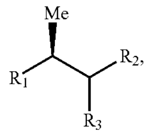

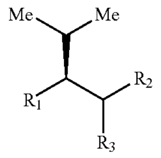

or absent, $X_5$ is

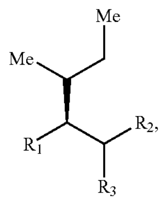

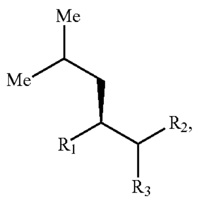

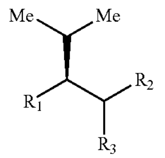

or absent, and $X_7$ is

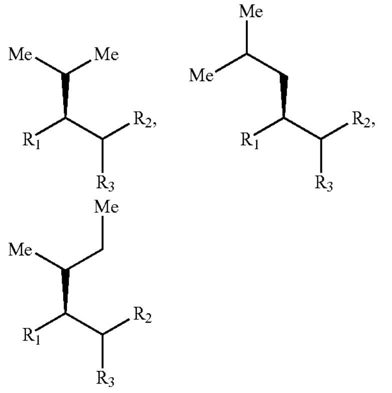

or absent, wherein said compound comprises a minimum of four of said consecutive $X_0$, $X_1$, $X_2$, $X_3$, $X_4$, $X_5$, $X_6$, and $X_7$, wherein $R^1$ is

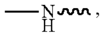

$NH_2$ or $NHR^{1'}$ where $R^{1'}$ is a suitable protecting group for an amine group, or a chromophore;

wherein is a point of attachment between said $X_1$ and $X_2$, $X_2$ and $X_3$, $X_3$ and $X_4$, $X_4$ and $X_5$, $X_5$ and $X_6$, or $X_6$ and $X_7$.

According to embodiments, the $X_0$ group reflects amino acids Arginine (Arg, R) or Lysine (Lys, K), the $X_1$ group reflects amino acids Leucine (Leu, L) or Isoleucine (Ile, I), the $X_2$ group reflects amino acids Lysine (Lys, K) or Arginine (Arg, R), the $X_3$ and $X_4$ groups reflects amino acids Glycine (Gly, G) or Alanine (Ala, A), the $X_5$ group reflects amino acids Lysine (Lys, K) or Arginine (Arg, R), the $X_6$ group reflects amino acids Isoleucine (Ile, I) or Leucine (Leu, L), and the $X_7$ group reflects amino acid Valine (Val, V).

According to another embodiment, the compound of formula II may be a compound of formula IIa IIa

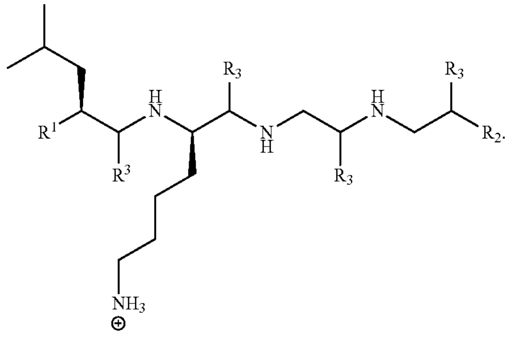

According to another embodiment, the compound of formula II may be a compound of formula IIb IIb

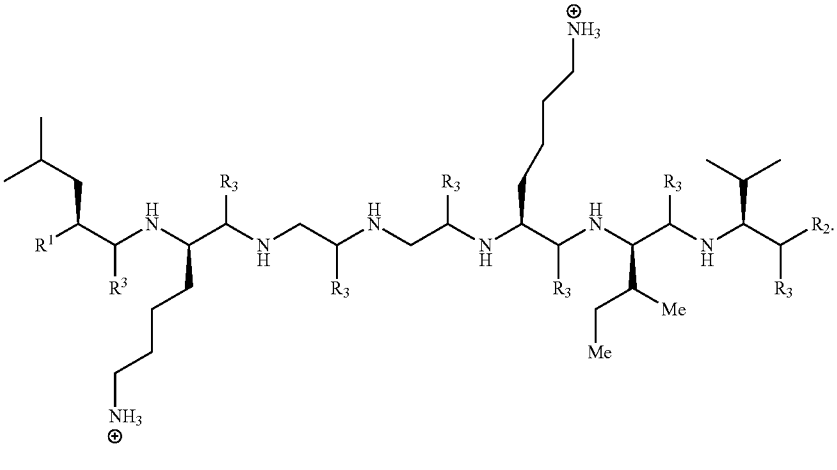

$R^2$ is OH or $OR^{3'}$, where $R^{3'}$ is a or a suitable protecting group for a hydroxyl group, or a chromophore, $R^3$ is =O, —OH or absent;

In the compound of formulae IIa and IIb, $R^1$ and are as defined above.

According to another embodiment, the compound of formula II may be a compound wherein $R_1$ is $NH_2$, $R_2$ is OH, and $R_3$ is =O.

According to another embodiment, the compound of formula II is
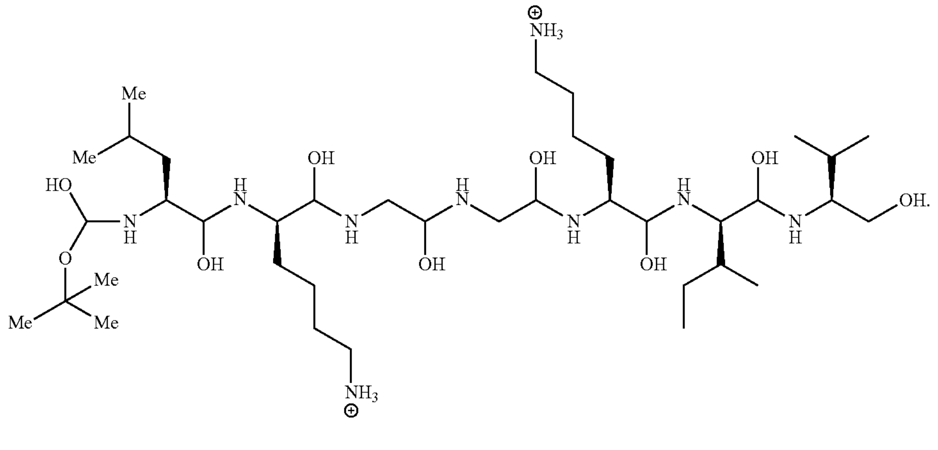 [SMILES: CCC(C)[C@@H](NC(O)[C@H](CCCC[NH3+])NC(O)CNC(O)CNC(O)[C@@H](CCCC[NH3+])NC(O)[C@H](CC(C)C)NC(O)OC(C)(C)C)C(O)N[C@H](CO)C(C)C]
According to another embodiment, the compound of formula II is
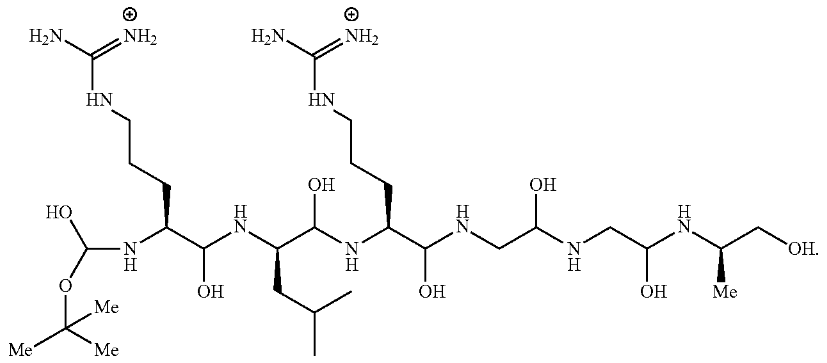 [SMILES: CC(C)C[C@@H](NC(O)[C@H](CCCNC(N)=[NH2+])NC(O)OC(C)(C)C)C(O)N[C@@H](CCCNC(N)=[NH2+])C(O)NCC(O)NCC(O)N[C@H](C)CO]
According to another embodiment, the compound of formula II is:
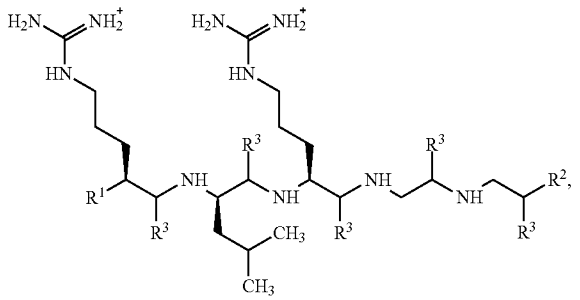
wherein
$R^1$ is —$NH_2$,
$R^2$ is —OH; and
$R^3$ is absent.
According to another embodiment, the compound of formula II is:
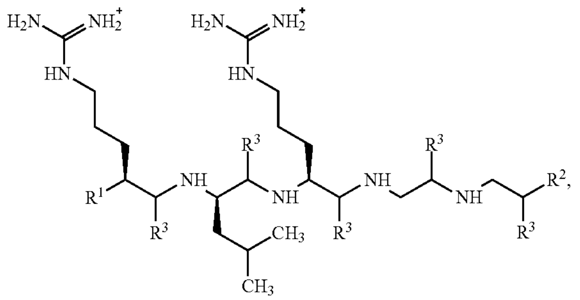
wherein
$R^1$ is —$NH_2$,
$R^2$ is —OH; and
$R^3$ is —OH.

According to another embodiment, the compound of formula II is:

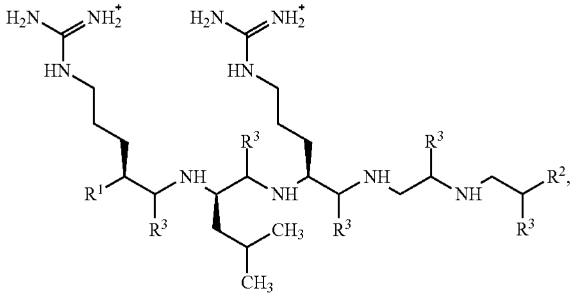

wherein $R^1$ is —$NH_2$, $R^2$ is —OH; and $R^3$ is =O.

According to another embodiment, the compound of formula II is:

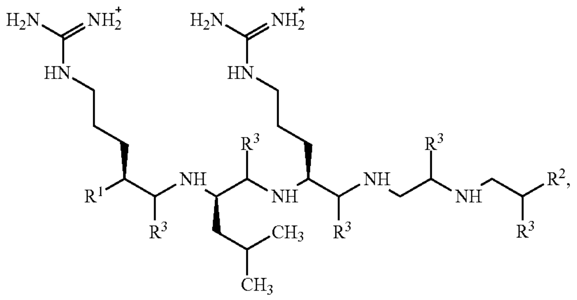

wherein $R^1$ is —$NH_2$;

$R^2$ is —$OR^{3'}$, where $R^{3'}$ is 7-Amino-4-methylcoumarin (AMC); and $R^3$ is absent.

According to another embodiment, the compound of formula II is:

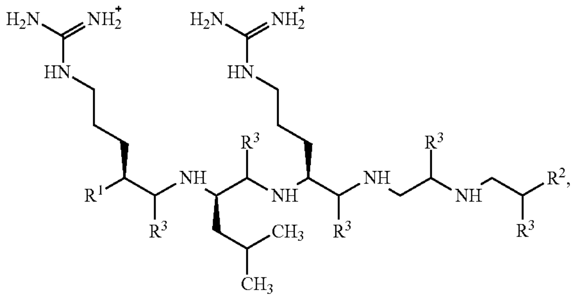

wherein $R^1$ is —$NH_2$;

$R^2$ is —$OR^{3'}$, where $R^{3'}$ is 7-Amino-4-methylcoumarin (AMC); and $R^3$ is —OH.

According to another embodiment, the compound of formula II is:

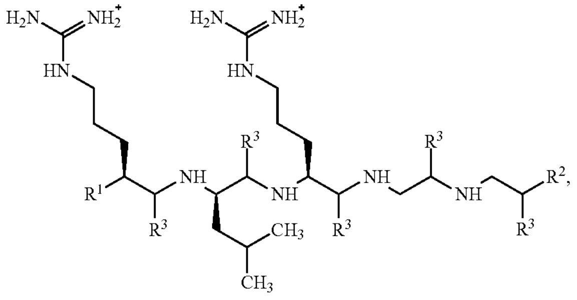

wherein $R^1$ is —$NHR^{1'}$, where $R^{1'}$ is carbobenzyloxy (Cbz);

$R^2$ is —$OR^{3'}$, where $R^{3'}$ is 7-Amino-4-methylcoumarin (AMC); and $R^3$ is absent.

According to another embodiment, the compound of formula II is:

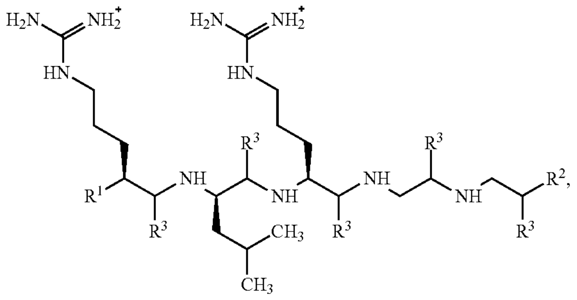

wherein $R^1$ is —$NHR^{1'}$, where $R^{1'}$ is carbobenzyloxy (Cbz);

$R^2$ is —$OR^{3'}$, where $R^{3'}$ is 7-Amino-4-methylcoumarin (AMC); and $R^3$ is —OH.

According to another embodiment, the compound of formula II is:

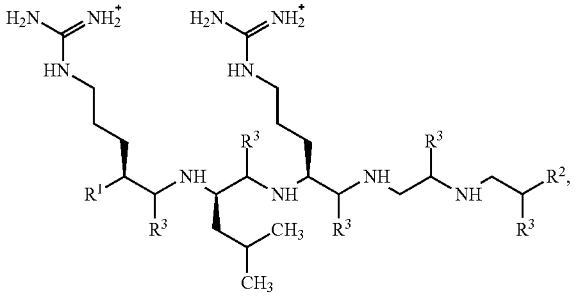

wherein $R^1$ is —$NHR^{1'}$, where $R^{1'}$ is carbobenzyloxy (Cbz);

$R^2$ is —$OR^{3'}$, where $R^{3'}$ is carbobenzyloxy (Cbz); and $R^3$ is absent.

According to another embodiment, the compound of formula II is:

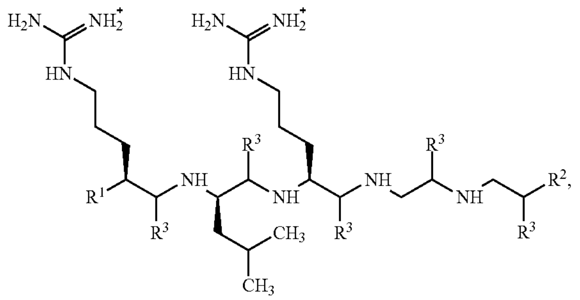

wherein $R^1$ is —$NHR^{1'}$, where $R^{1'}$ is carbobenzyloxy (Cbz);

$R^2$ is —$OR^{3'}$, where $R^{3'}$ is carbobenzyloxy (Cbz); and $R^3$ is —OH.

According to another embodiment, the compound of formula II is:

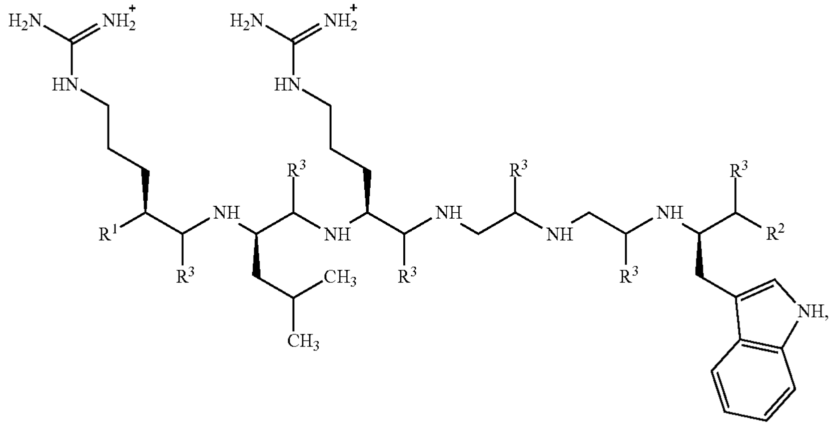

wherein $R^1$ is —$NHR^{1'}$, where $R^{1'}$ is carbobenzyloxy (Cbz);

$R^2$ is —OH; and $R^3$ is absent.

According to another embodiment, the compound of formula II is:

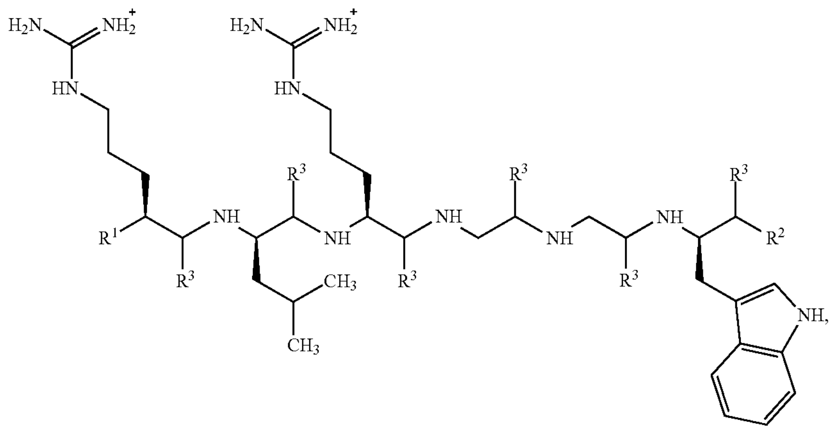

wherein $R^1$ is —$NHR^{1'}$, where $R^{1'}$ is carbobenzyloxy (Cbz);

$R^2$ is —OH; and $R^3$ is —OH.

According to another embodiment, the compound of formula II is:

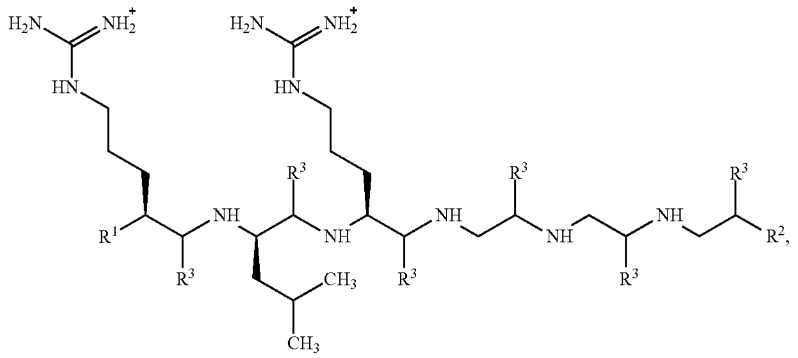

wherein $R^1$ is —$NHR^{1'}$, where $R^{1'}$ is carbobenzyloxy (Cbz);

$R^2$ is —$OR^{3'}$, where $R^{3'}$ is 7-Amino-4-methylcoumarin (AMC); and $R^3$ is absent.

According to another embodiment, the compound of formula II is:

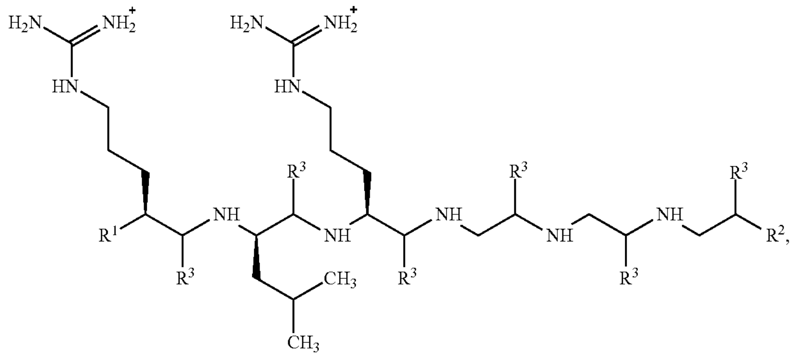

wherein $R^1$ is —$NHR^{1'}$, where $R^{1'}$ is carbobenzyloxy (Cbz);

$R^2$ is —$OR^{3'}$, where $R^{3'}$ is 7-Amino-4-methylcoumarin (AMC); and $R^3$ is —OH.

According to another embodiment, the compound of formula II is:

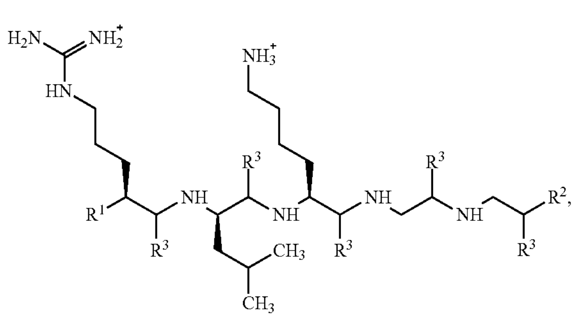

wherein $R^1$ is —$NH_2$;

$R^2$ is —OH; and $R^3$ is =O.

According to another embodiment, the compound of formula II is:

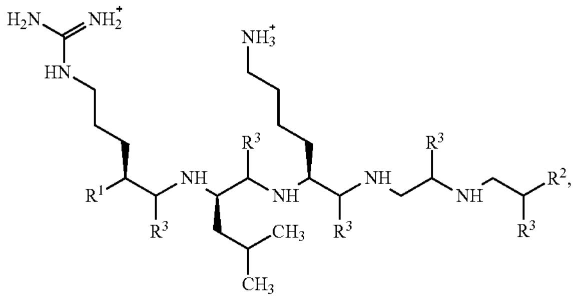

wherein $R^1$ is $-NH_2$;

$R^2$ is $-OH$; and $R^3$ is $=O$.

According to another embodiment, the compound of formula II is:

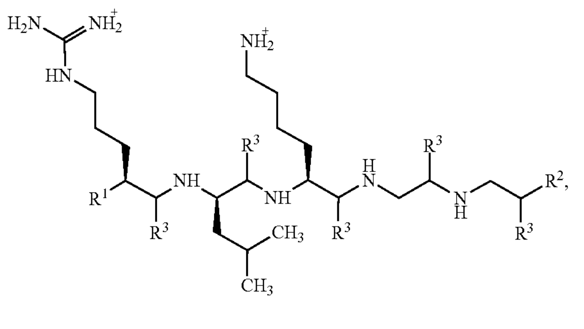

wherein $R^1$ is $-NH_2$;

$R^2$ is $-OH$; and $R^3$ is $-OH$.

The suitable protecting group for an amine group may be selected from the group consisting of carbobenzyloxy (Cbz), p-Methoxybenzyl carbonyl (MeOZ), tert-Butyloxycarbonyl (BOC), 9-Fluorenylmethyloxycarbonyl (Fmoc), acetyl (Ac), benzoyl (Bz), benzyl (Bn), p-Methoxybenzyl (PMB), 3,4-Dimethoxybenzyl (DMPM), p-Methoxyphenyl (PMP), tosyl (Ts), troc (trichloroethyl chloroformate), 4-nitrobenzene-1-sulfonyl chloride (Nosyl) and 2-Nitrophenylsulfenyl (Nps).

The suitable protecting group for a hydroxyl group may be selected from the group consisting of alkyl, acetyl (Ac), benzoyl (Bz), benzyl (Bn), β-Methoxyethoxymethyl ether (MEM), [bis-(4-methoxyphenyl)phenylmethyl] (DMT), methoxymethyl ether (MOM), methoxytrityl [(4-methoxyphenyl)diphenylmethyl] (MMT), p-Methoxybenzyl ether (PMB), methylthiomethyl ether, pivaloyl (Piv), tetrahydropyranyl (THP), tetrahydrofuran (THF), trityl (triphenylmethyl, Tr), trimethylsilyl (TMS), tertiobutyldiphenylsilyl (TBDPS), tert-butyldimethylsilyl (TBDMS), tri-iso-propylsilyloxymethyl (TOM), triisopropylsilyl (TIPS), methyl ethers, and ethoxyethyl ethers (EE).

The chromophore may be 7-Amino-4-methylcoumarin (AMC).

According to embodiments, in the compounds of the present invention, the suitable protecting group for an amine group are selected from the group consisting of carbobenzyloxy (Cbz), p-Methoxybenzyl carbonyl (MeOZ), tert-Butyloxycarbonyl (BOC), 9-Fluorenylmethyloxycarbonyl (Fmoc), acetyl (Ac), benzoyl (Bz), benzyl (Bn), p-Methoxybenzyl (PMB), 3,4-Dimethoxybenzyl (DMPM), p-Methoxyphenyl (PMP), tosyl (Ts), troc (trichloroethyl chloroformate), 4-nitrobenzene-1-sulfonyl chloride (Nosyl) and 2-Nitrophenylsulfenyl (Nps).

According to embodiments, in the compounds of the present invention, the suitable protecting group for a hydroxyl group are selected from the group consisting of alkyl, acetyl (Ac), benzoyl (Bz), benzyl (Bn), p-Methoxyethoxymethyl ether (MEM), [bis-(4-methoxyphenyl)phenylmethyl] (DMT), methoxymethyl ether (MOM), methoxytrityl [(4-methoxyphenyl)diphenylmethyl] (MMT), p-Methoxybenzyl ether (PMB), methylthiomethyl ether, pivaloyl (Piv), tetrahydropyranyl (THP), tetrahydrofuran (THF), sylil ethers such as trialkylsilyl, tertiobutyldiphenylsilyl (TBDPS), trityl (triphenylmethyl, Tr), trimethylsilyl (TMS), tert-butyldimethylsilyl (TBDMS), tri-iso-propylsilyloxymethyl (TOM), triisopropylsilyl (TIPS), methyl ethers, and ethoxyethyl ethers (EE).

The invention includes the compounds as shown, and also includes (where possible) individual diastereomers, enantiomers, and epimers of the compounds, and mixtures of diastereomers and/or enantiomers thereof including racemic mixtures. Although the specific stereochemistries disclosed herein are preferred, other stereoisomers, including diastereomers, enantiomers, epimers, and mixtures of these may also be useful in activating viral proteases. Inactive or less active diastereoisomers and enantiomers are useful for scientific studies relating to the enzyme target and the mechanism of activation.

Pharmaceutical Compositions

The compounds disclosed herein may be used in pharmaceutical compositions comprising (a) the compound(s) or pharmaceutically acceptable salts thereof and stereoisomers thereof, and (b) a pharmaceutically acceptable carrier. The compounds may be used in pharmaceutical compositions that include one or more other active pharmaceutical ingredients. The compounds may also be used in pharmaceutical compositions in which the compounds of Formula I or II or a pharmaceutically acceptable salt thereof and stereoisomers thereof, is the only active ingredient.

According to an embodiment, the compounds of the present invention are inhibitors of viral proteases and are useful for inactivating these viral proteases in the treatment of viral infections. Such compounds may be useful in the treatment of viral infections such as the SARS CoV-2 which cause COVID-19.

According to another embodiment, the compounds of the present invention may be given directly to a patient in need of such treatment, using oral, intravenous, subcutaneous, sublingual, inhalation or intramuscular administration.

The term «composition» as used herein is intended to encompass a product comprising the specified ingredients in the specified amounts, as well as any product which results, directly or indirectly, from combination of the specified ingredients in the specified amounts. Such term in relation to pharmaceutical composition is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" or "acceptable" it is meant the carrier, diluent or excipient must be compatible with the other ingredients of the formulation and not deleterious to the recipient thereof.

Compounds of structural Formula I, structural Formula Ia, structural Formula II, structural Formula IIa, may contain one or more asymmetric centers and can thus occur as racemates and racemic mixtures, single enantiomers, diastereomeric mixtures and individual diastereomers. The present invention is meant to comprehend all such isomeric forms of the compounds of structural Formula I and/or structural Formula Ia.

Compounds of structural Formula I, structural Formula Ia, structural Formula II, and/or structural Formula IIa may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural Formula I, structural Formula Ia, structural Formula II, and/or structural Formula IIa may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of generic Formula I, structural Formula Ia, structural Formula II, and/or structural Formula IIa the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I, structural Formula Ia, structural Formula II, and/or structural Formula IIa. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I, structural Formula Ia, structural Formula II, and/or structural Formula IIa can be prepared without undue experimentation by conventional techniques well known to those skilled in the art or by processes analogous to those described in the Schemes and Examples herein using appropriate isotopically-enriched reagents and/or intermediates.

Salts and Formulations

It will be understood that, as used herein, references to the compounds of structural Formula I, structural Formula Ia, structural Formula II, and/or structural Formula IIa are meant to also include the pharmaceutically acceptable salts, and also salts that are not pharmaceutically acceptable when they are used as precursors to the free compounds or their pharmaceutically acceptable salts or in other synthetic manipulations. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural Formula I, structural Formula Ia, structural Formula II, and/or structural Formula IIa are included in the present invention as well.

According to an embodiment, the compounds of structural Formula I, structural Formula Ia, structural Formula II, and/or structural Formula IIa may be included in various formulations for use as medicaments. Formulations for oral use may be presented as well-known "dosage forms" or solid dosage form", which is intended to mean pill, tablet, prills, granules, pellets, beads, multiparticulates, capsules, or suppository (rectal, vaginal) device for the delivery of an active ingredient. This also includes hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxy-benzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an I atomiser using electrohydrodynamics to produce a fine mist), or nebuliser, with or without the use of a suitable propellant, such as 1, 1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns).

This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from log to 20 mg of the compound of the invention per actuation and the actuation volume may vary from 11 to 1001. A typical formulation may comprise a compound of formula I, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 fig to 10 mg of the compound of formula I. The overall daily dose will typically be in the range 1 lag to 10 mg which may be administered in a single dose or, more usually, as divided doses throughout the day.

Compounds of structural Formula I, structural Formula Ia, structural Formula II, and/or structural Formula IIa may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of structural Formula I, structural Formula Ia, structural Formula II, and/or structural Formula IIa are employed. (For purposes of this application, topical application shall include mouth washes and gargles.)

Utilities

According to an embodiment, the inhibitors of viral protease may improve and may have utility in preventing or treating viral infections, particularly SARS CoV 2 infection.

One aspect of the invention provides a method of treating or preventing a viral infection in a subject in need thereof comprising administering a therapeutically effective amount a compound of Formula I, structural Formula Ia, structural Formula II, and/or structural Formula IIa, or a pharmaceutically acceptable salt thereof, or the composition of the present invention, to the subject.

A second aspect of the invention provides the use of a compound of Formula I, structural Formula Ia, structural Formula II, and/or structural Formula IIa, or a pharmaceutically acceptable salt thereof for the manufacture of a medicament for treatment or prevention of a viral infection in a subject in need thereof.

A third aspect of the invention provides the use of a compound of structural Formula I, structural Formula Ia, structural Formula II, and/or structural Formula IIa, or a pharmaceutically acceptable salt thereof, or the composition of the present invention, for treatment or prevention of a viral infection in a subject in need thereof.

A fourth aspect of the invention provides the compound of compound of structural Formula I, structural Formula Ia, structural Formula II, and/or structural Formula IIa, or a pharmaceutically acceptable salt thereof for use in the treatment or prevention of a viral infection in a subject in need thereof.

In the use, the compound for use, or the method of the present invention, the viral infection may be a SARS-CoV-2 infection.

The compounds of formula I, or pharmaceutically acceptable salts thereof, and stereoisomers thereof have the general formula:

(I)

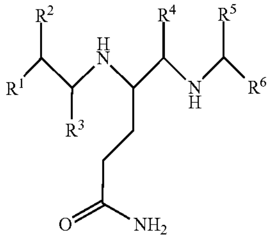

wherein $R^1$ is $NH_2$ or $NHR^{1'}$ where $R^{1'}$ is a suitable protecting group for an amine group;

$R^2$ is selected from the group consisting of

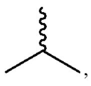, 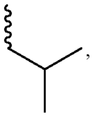, 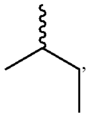, and 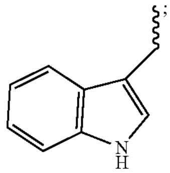;

$R^3$ is =O or absent;

$R^4$ is =O, —SH, or absent;

$R^5$ is absent or is selected from the group consisting of —$CH_3$, —$CH_2$—OH, and

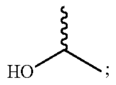;

and $R^6$ is —C(O)OH or —C(O)$OR^{6'}$, where $R^{6'}$ is a or a suitable protecting group for a hydroxyl group, wherein 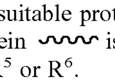 is a point of attachment with the $R^1$, $R^2$, $R^3$, $R^4$, $R^5$ or $R^6$.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

The present invention will be more readily understood by referring to the following examples which are given to illustrate the invention rather than to limit its scope.

Example 1

Preparation of Compounds of Formula I

Synthetic methods for preparing the compounds of the present invention are illustrated in the following Schemes, Methods, and Examples. Starting materials are commercially available or may be prepared according to procedures known in the art or as illustrated herein. In some cases the order of carrying out the foregoing reaction schemes may be varied to facilitate the reaction or to avoid unwanted reaction products. The compounds of the invention are illustrated by means of the specific examples shown below. However, these specific examples are not to be construed as forming the only genus that is considered as the invention. These examples further illustrate details for the preparation of the compounds of the present invention. Those skilled in the art will readily understand that known variations of the conditions and processes of the following preparative procedures can be used to prepare these compounds. All temperatures are in degrees Celsius unless otherwise noted. Mass spectra (MS) were measured by electrospray ion-mass spectroscopy (ESI). $^1H$ NMR spectra were recorded on Bruker instruments at 400 or 500 MHz.

List of Abbreviations

Alk=alkyl
Ar=aryl
BINAP=2, 2'-bis(diphenylphosphino)-1,1'-binaphthalene
Boc=tert-butoxycarbonyl
br=broad
$CH_2Cl_2$=dichloromethane
d=doublet
DBU=1,8-diazabicyclo[5.4.0]undec-7-ene
DEAD=diethyl azodicarboxylate
DIBAL=diisobutylaluminum hydride
DIPEA=N,N-diisopropylethylamine
DMF=dimethylformamide
DMSO=dimethyl sulfoxide ESI=electrospray ionization
EtOAc=ethyl acetate
h=hours
HATU=O-(7-azabenzotriazol-1-yl)-N,N,N',N'-tetramethyluronium hexafluorophosphate
HOAc=acetic acid
Hunig's base=diisopropylethylamine
LiOH=lithium hydroxide
m=multiplet
MeCN=acetonitrile
MeOH=methyl alcohol
MeTHF=2-methyltetrahydrofuran
$MgSO_4$=magnesium sulfate
min=minutes
MS=mass spectroscopy
MTBE=methyl tert-butyl ether
NaOH=sodium hydroxide
$Na_2SO_4$=sodium sulfate
NMP=N-methyl 2-pyrrolidinone
NMR=nuclear magnetic resonance spectroscopy
PG=protecting group
Ph=phenyl
rt=room temperature
s=singlet
t=triplet
TFA=trifluoroacetic acid
TFAA=trifluoroacetic anhydride
THF=tetrahydrofuran
TMEDA=N,N,N',N'tetramethylethylenediamine Method A: Synthesis of a Competitive Inhibitor Step 1: Protection of the Amino Group on Leucine with Boc Anhydride (tert-butoxycarbonyl).

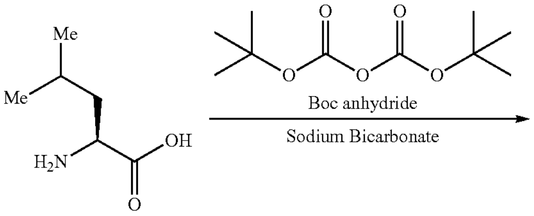

(I)
Leucine

-continued

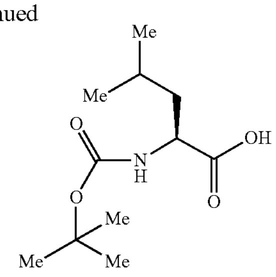

(II)
Boc-Leucine

Protection of the Amine can also be accomplished in Acetonitrile solution using 4-dimethylaminopyridine (DMAP) as the base.

Step 2: Activation of the carboxylic acid group on Boc-Leucine with DCC (N,N'-Dicyclohexylcarbodiimide).

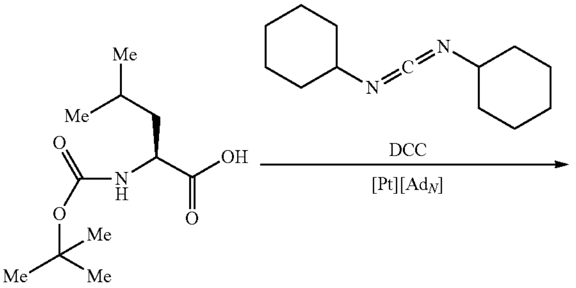

(II)
Boc-Leucine

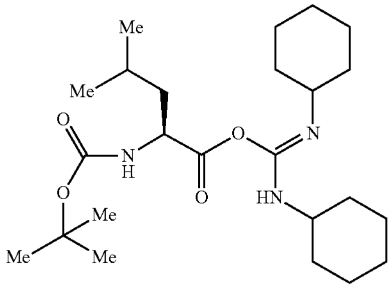

(III)
Boc-Leucine-DCC

Step 3: Addition of Glutamine by peptide bond formation.

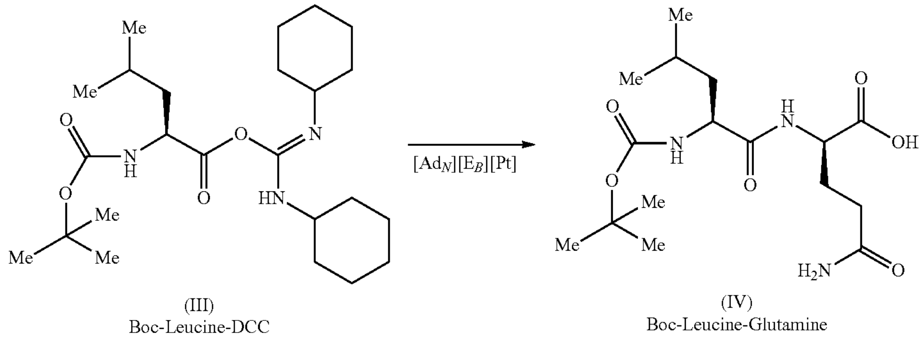

(III)
Boc-Leucine-DCC
+

(IV)
Boc-Leucine-Glutamine
+

-continued
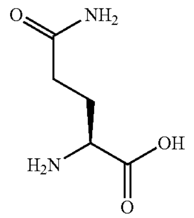
Glutamine
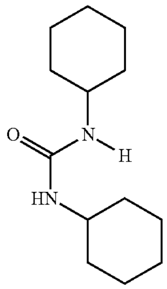
Step 4: Activation of the carboxylic acid group on Boc-Leucine-Glutamine with DCC.
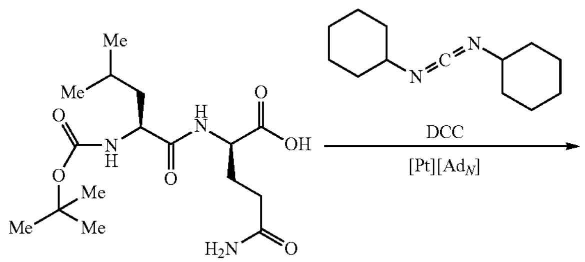
(IV)
Boc-Leucine-Glutamine
-continued
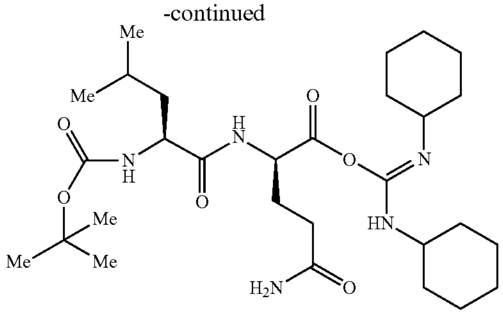
(V)
Boc-Leucine-Glutamine-DCC
Step 5: Addition of Serine to Boc-Leucine-Glutamine by peptide bond formation.
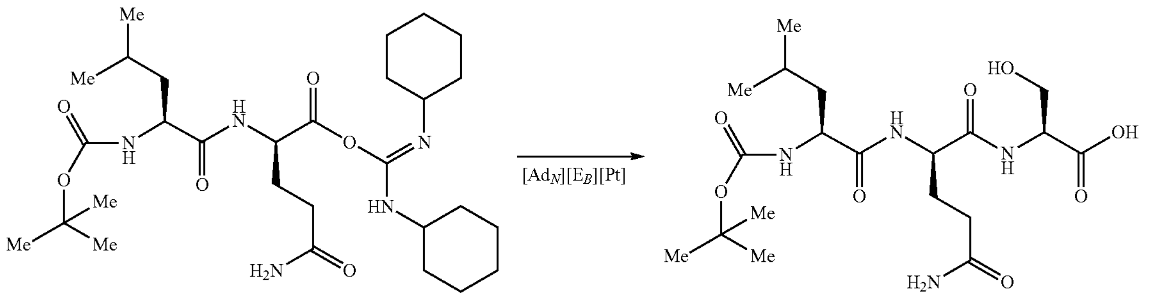
(V)
Boc-Leucine-Glutamine-DCC
+
(VI)
Boc-Leucine-Glutamine-Serine-COOH
+
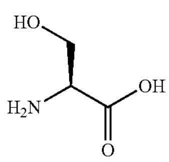
Serine
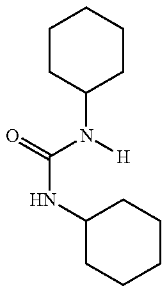

Step 6: Reduction of the Two Carbonyl Carbon Using $NaBH_4$.

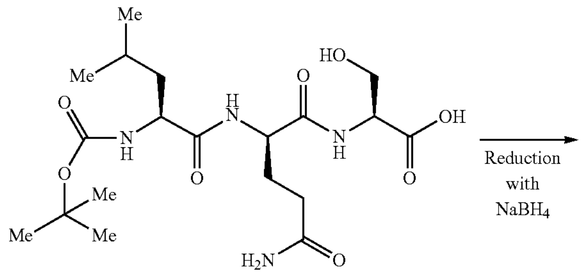

(VI)
Boc-Leucine-Glutamine-Serine-COOH

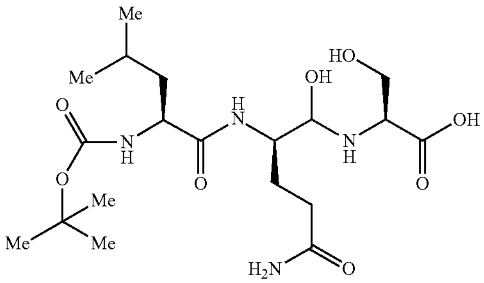

(VII)
Boc-Leucine (reduced carbony)-Glutamine (reduced carbony)-Serine-COOH

Method B: Synthesis of a Non-Competitive Inhibitor

Step 1: Protection of the Amino Group on Leucine with Boc Anhydride (tert-butoxycarbonyl).

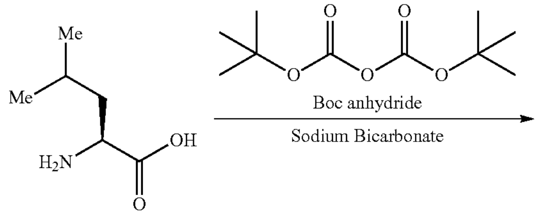

(I)
Leucine

-continued

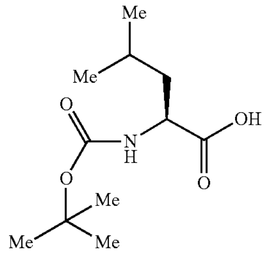

(II)
Boc-Leucine

Protection of the Amine can also be accomplished in Acetonitrile solution using 4-dimethylaminopyridine (DMAP) as the base.

Step 2: Activation of the carboxylic acid group on Boc-Leucine with DCC (N,N'-Dicyclohexylcarbodiimide).

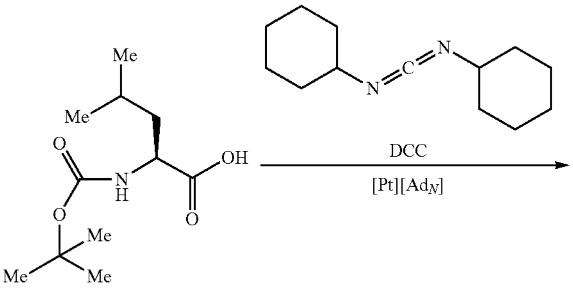

(II)
Boc-Leucine

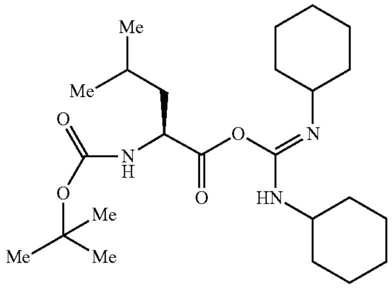

(III)
Boc-Leucine-DCC

Step 3: Addition of Glutamine by peptide bond formation.

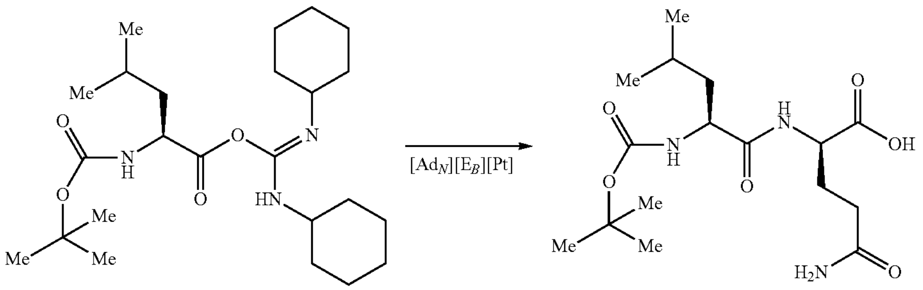

(III)
Boc-Leucine-DCC (IV)
Boc-Leucine-Glutamine

+

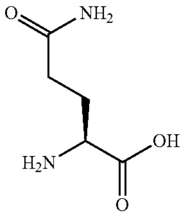

Glutamine

+

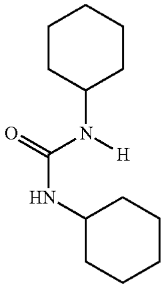

Step 4: reduction of carbonyl group in the peptide bond between Boc-Leucine and Glutamine.

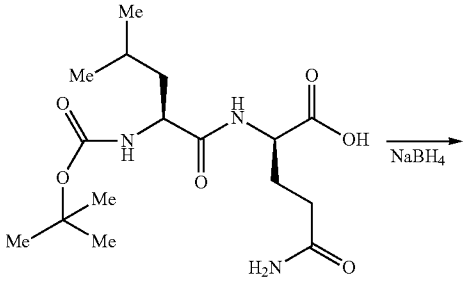

(IV)
Boc-Leucine-Glutamine

Step 5: activation of the carboxylic acid on the reduced Boc-Leucine-Glutamine with DCC.

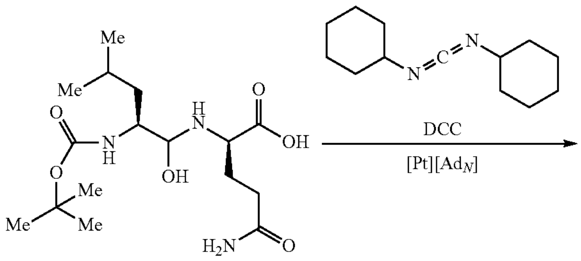

(VIII)
Reduced Boc-Leucine-Glutamine

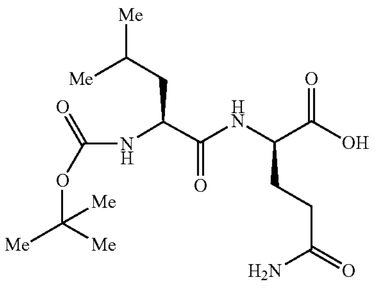

(VIII)
Reduced Boc-Leucine-Glutamine

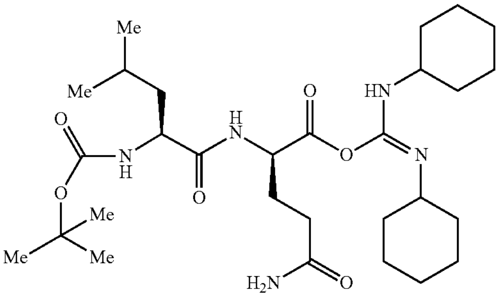

(IX)
Reduced Boc-Leucine-Glutamine-Activated

Step 6: addition of serine to the reduced Boc-Leucine-Glutamine-activated by peptide bond condensation.

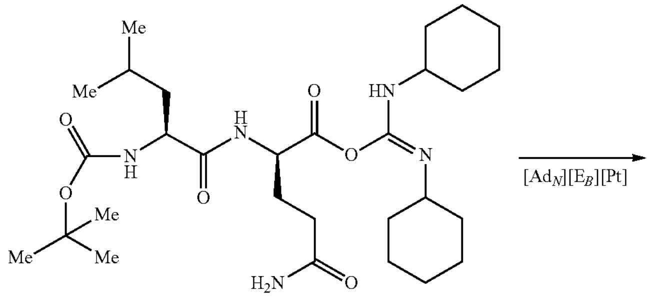

(IX)
Reduced Boc-Leucine-Glutamine-Activated

+

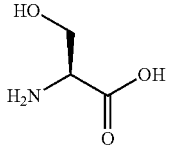

Serine

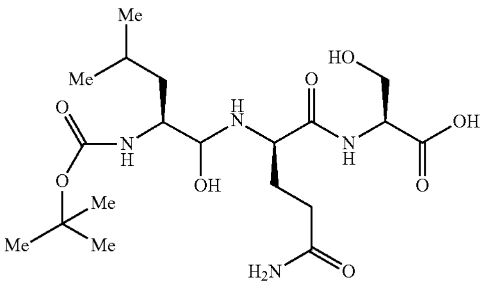

(X)
Boc-Leucine (reduced carbonyl)-Glutamine-Serine-COOH

+

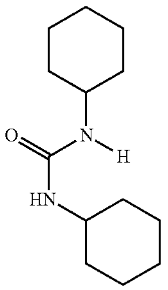

Step 7: addition of sulfhydryl group to the carbonyl carbon between the reduced-Boc-Leucine-Glutamine and Serine Using sodium sulfide ($Na_2S$ or $Na_2S{\cdot}9H_2O$).

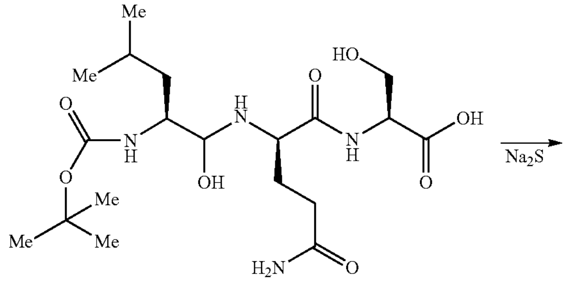

(X)
Boc-Leucine (reduced carbonyl)-Glutamine-Serine-COOH

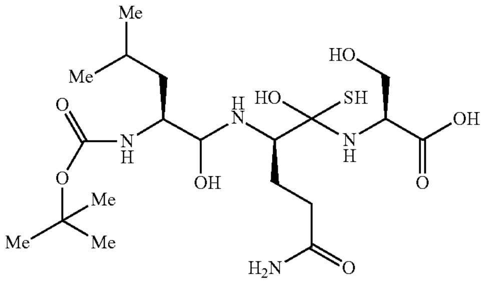

(XI)
Boc-Leucine (reduced carbonyl)-Glutamine-(OH)(SH)-Serine-COOH

Example 2

Assays for Measuring Biological Activity

The effective concentration of a compound of Formula I for use in inhibiting viral protease may be determined through an in vitro titration assays involving enzyme kinetics studies using purified coronavirus protease and monitoring the levels of enzyme inhibition. Additional in vitro studies could involve determination of the levels of viral replication using mammalian cells infected with coronavirus. The lowest concentration that provides maximal inhibition of protease activity or viral replication in the absence of cellular toxicity will be dependent on the compound's intrinsic potency and its ability to inhibit coronavirus protease. This optimal concentration is then used to treat mice or rats infected with coronavirus to further determine inhibition activity levels and appropriate in vivo concentrations. Useful concentrations range from 1 nM to 1 mM in aqueous buffer or cell media. Preferably, the concentration used is between 1 μM and 100 μM.

Example 3

Preparation of Compounds of Formula II

Synthetic methods for preparing the compounds of the present invention are illustrated in the following Schemes, Methods, and Examples. Starting materials are commercially available or may be prepared according to procedures known in the art or as illustrated herein. In some cases the order of carrying out the foregoing reaction schemes may be varied to facilitate the reaction or to avoid unwanted reaction products. The compounds of the invention are illustrated by means of the specific examples shown below. However, these specific examples are not to be construed as forming the only genus that is considered as the invention. These examples further illustrate details for the preparation of the compounds of the present invention. Those skilled in the art will readily understand that known variations of the conditions and processes of the following preparative procedures can be used to prepare these compounds. All temperatures are in degrees Celsius unless otherwise noted. Mass spectra (MS) were measured by electrospray ion-mass spectroscopy (ESI). $^1H$ NMR spectra were recorded on Bruker instruments at 400 or 500 MHz.

List of Abbreviations

Alk=alkyl
Ar=aryl
BINAP=2, 2'-bis(diphenylphosphino)-1,1'-binaphthalene
Boc=tert-butoxycarbonyl
br=broad
$CH_2Cl_2$=dichloromethane
d=doublet
DBU=1,8-diazabicyclo[5.4.0]undec-7-ene
DEAD=diethyl azodicarboxylate
DIBAL=diisobutylaluminum hydride
DIPEA=N,N-diisopropylethylamine
DMF=dimethylformamide
DMSO=dimethyl sulfoxide
ESI=electrospray ionization
EtOAc=ethyl acetate
h=hours
HATU=O-(7-azabenzotriazol-1-yl)-N,N,N',N'-tetramethyluronium hexafluorophosphate
HOAc=acetic acid
Hunig's base=diisopropylethylamine
LiOH=lithium hydroxide
m=multiplet
MeCN=acetonitrile
MeOH=methyl alcohol
MeTHF=2-methyltetrahydrofuran
$MgSO_4$=magnesium sulfate
min=minutes
MS=mass spectroscopy
MTBE=methyl tert-butyl ether
NaOH=sodium hydroxide
$Na_2SO_4$=sodium sulfate
NMP=N-methyl 2-pyrrolidinone
NMR=nuclear magnetic resonance spectroscopy
PG=protecting group
Ph=phenyl
rt=room temperature
s=singlet
t=triplet
TFA=trifluoroacetic acid
TFAA=trifluoroacetic anhydride
THF=tetrahydrofuran
TMEDA=N,N,N',N'-tetramethylethylenediamine Method A: Synthesis of a PLpro Competitive Inhibitor Step A1: Protection of the amino group on Leucine with Boc Anhydride (tert-butoxycarbonyl).

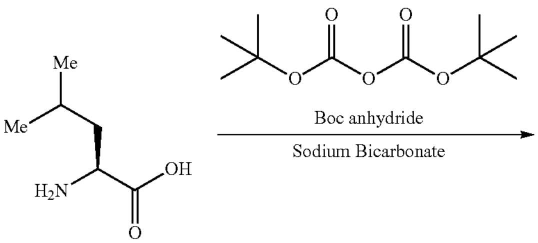

[I]
Leucine

-continued

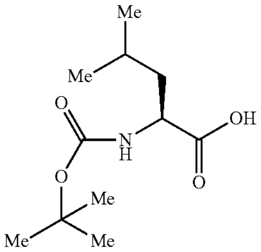

[II]
Boc-Leucine

Protection of the Amine can also be accomplished in Acetonitrile solution using 4-dimethylaminopyridine (DMAP) as the base.

Step A2: Activation of the carboxylic acid group on Boc-Leucine with DCC (N,N'-Dicyclohexylcarbodiimide).

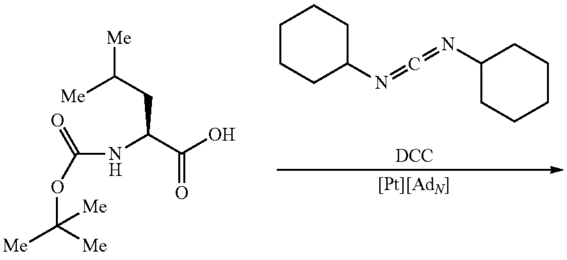

[II]
Boc-Leucine

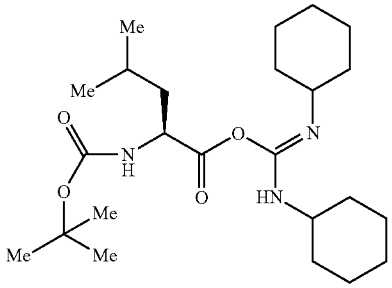

[III]
Boc-Leucine-DCC

Step A3: Addition of Lysine by peptide bond formation.
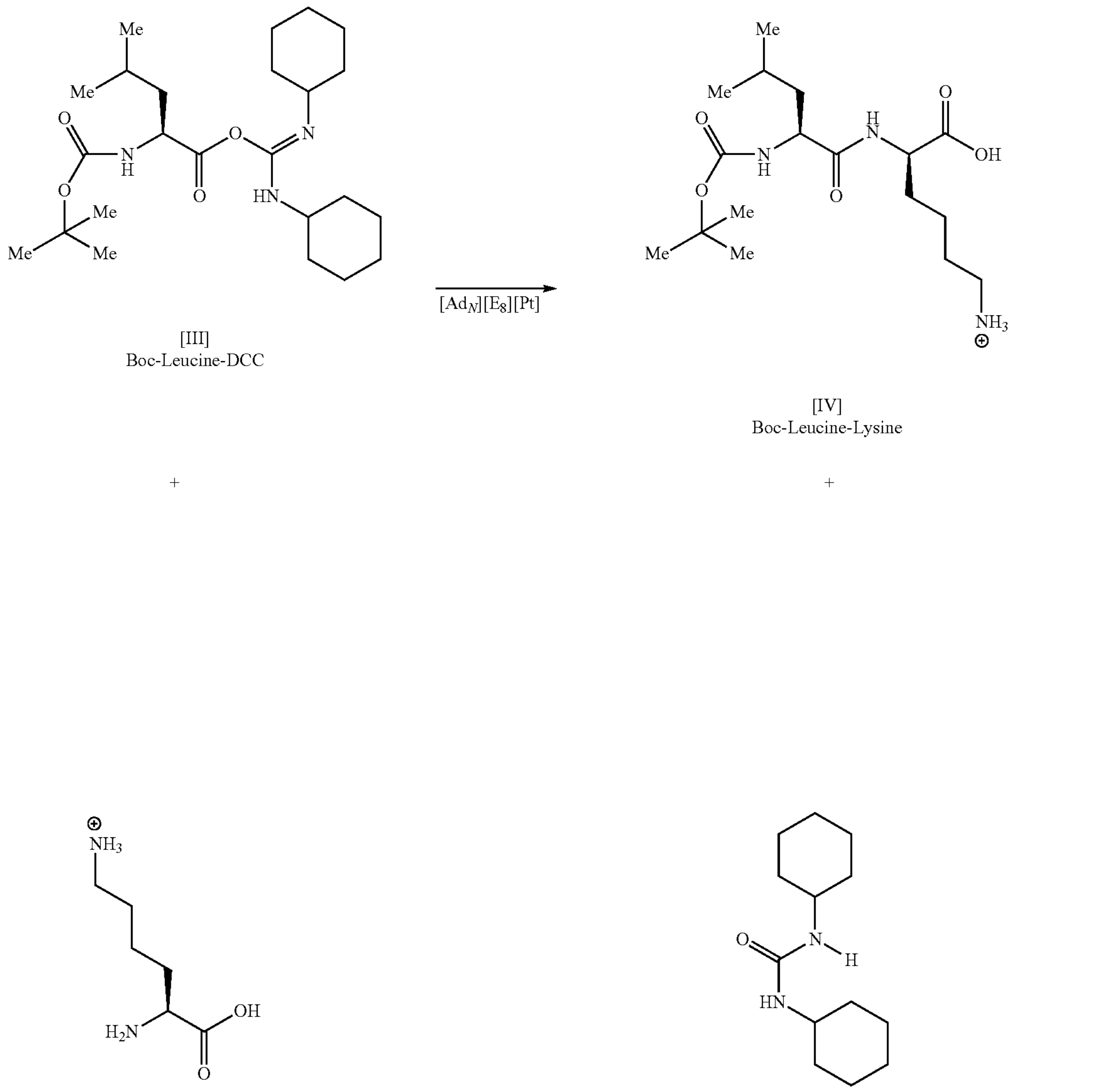
[III]
Boc-Leucine-DCC
+
Lysine
[IV]
Boc-Leucine-Lysine
+
Step A4: Activation of the carboxylic acid group on Boc-Leucine-Lysine with DCC.
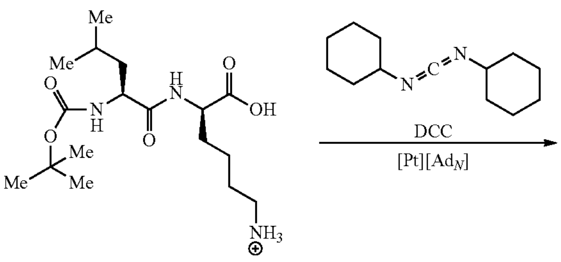
[IV]
Boc-Leucine-Lysine
-continued
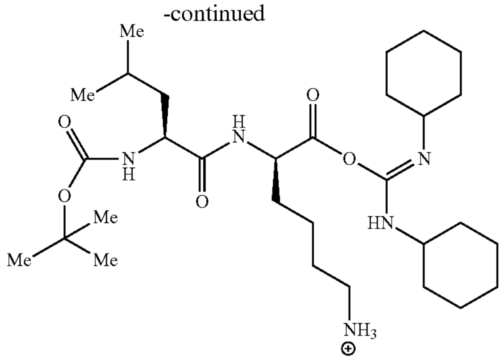
[V]
Boc-Leucine-Lysine-DCC Step A5: Addition of Glycine to Boc-Leucine-Lysine by peptide bond formation.
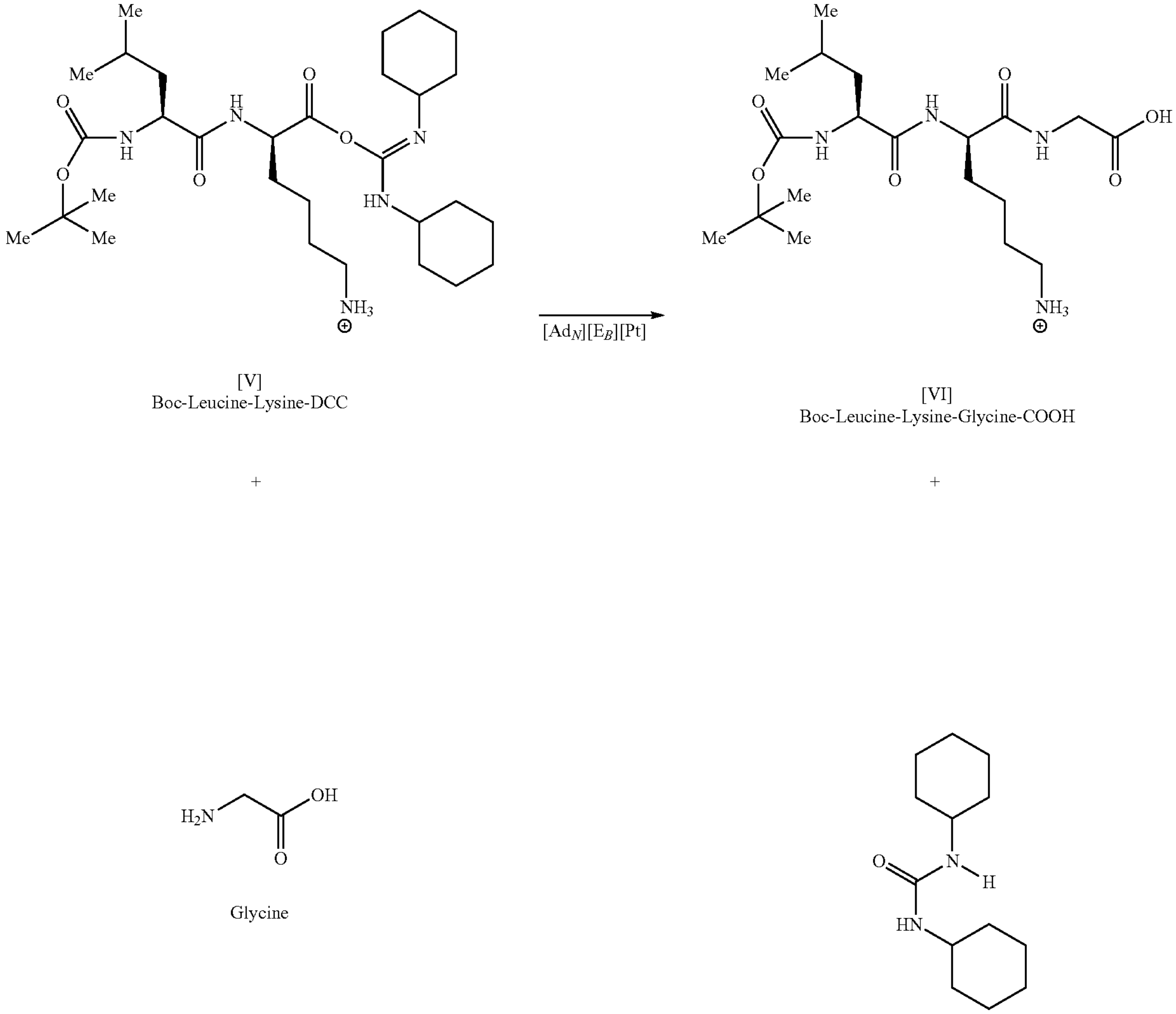
[V]
Boc-Leucine-Lysine-DCC
+
Glycine
[VI]
Boc-Leucine-Lysine-Glycine-COOH
+
Step A6: Activation of the carboxylic acid group on Boc-Leucine-Lysine-Glycine with DCC.
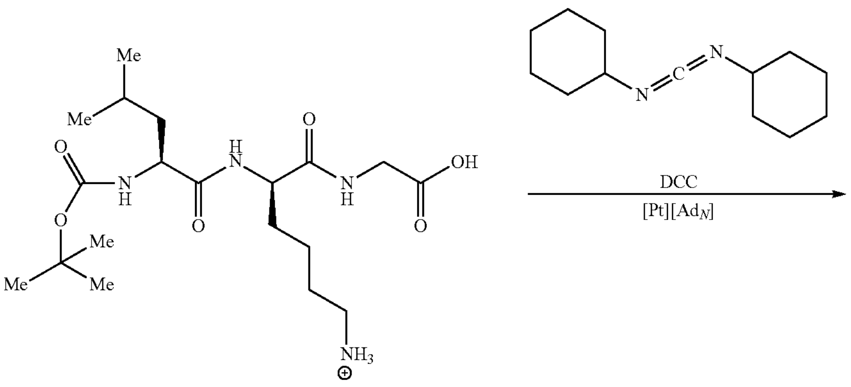
[VI]
Boc-Leucine-Lysine-Glycine-COOH -continued
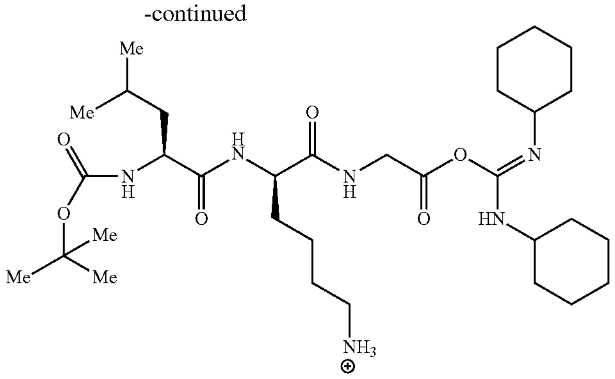
[VII]
Boc-Leucine-Lysine-Glycine-DCC
Step A7: Addition of Glycine to Boc-Leucine-Lysine-Glycine-DCC by peptide bond formation.
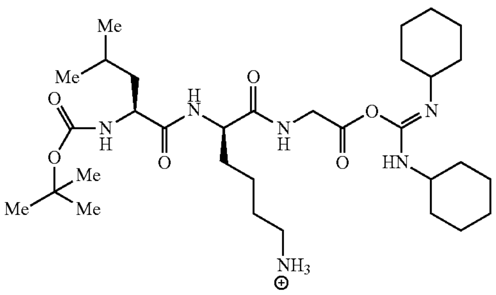
[VII]
Boc-Leucine-Lysine-Glycine-DCC
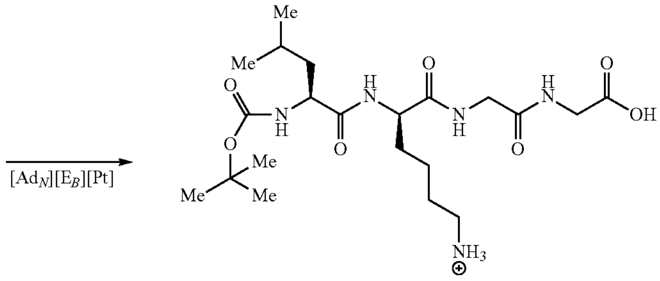
[VIII]
Boc-Leucine-Lysine-Glycine-Glycine-COOH
+
+
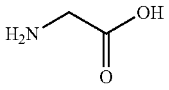
Glycine
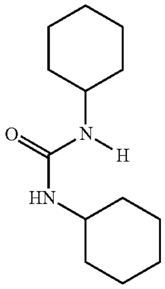

Step A8: Activation of Boc-Leucine-Lysine-Glycine-Glycine with DCC.
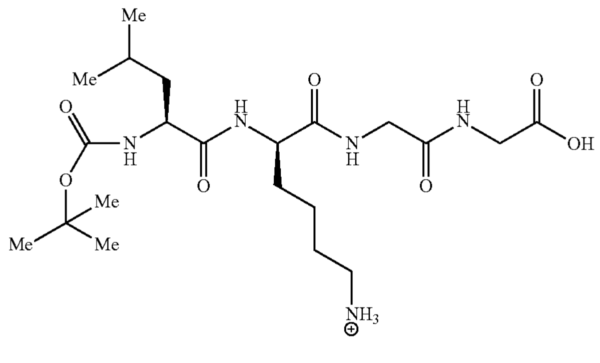
[VIII]
Boc-Leucine-Lysine-Glycine-Glycine-COOH
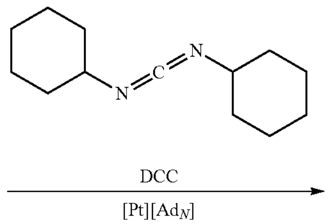
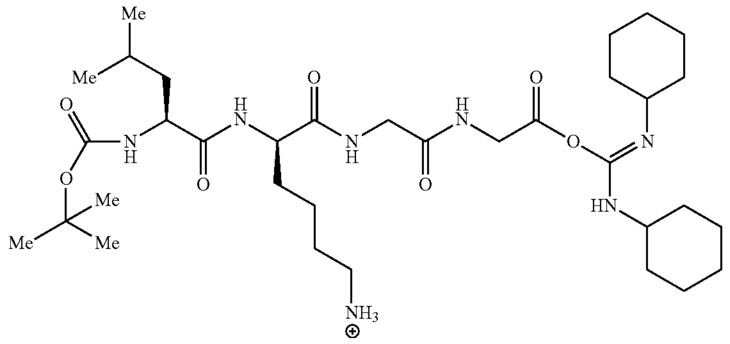
[IX]
Boc-Leucine-Lysine-Glycine-Glycine-DCC
Step A9: Addition of Lysine to Boc-Leucine-Lysine-Glycine-Glycine-DCC by peptide bond formation.
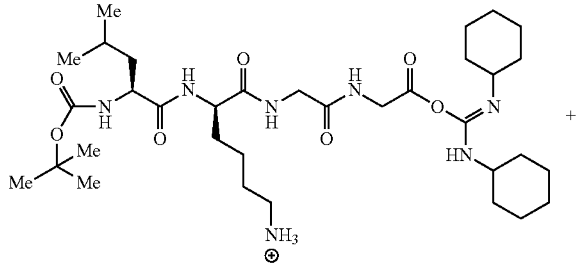
[IX]
Boc-Leucine-Lysine-Glycine-Glycine-DCC
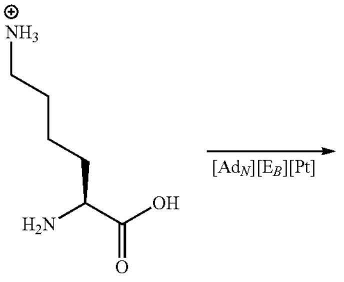
Lysine
-continued
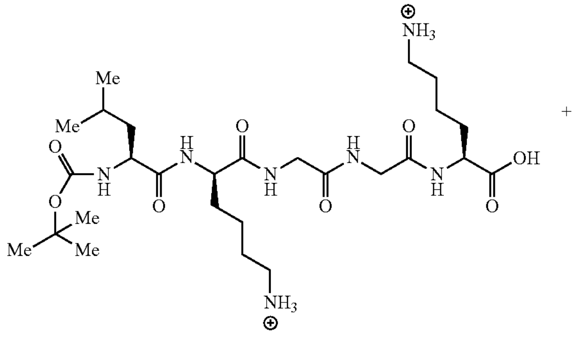
[X]
Boc-Leucine-Lysine-Glycine-Glycine-Lysine-COOH
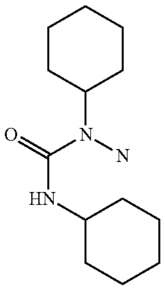

Step A10: Activation of Boc-Leucine-Lysine-Glycine-Glycine-Lysine with DCC.
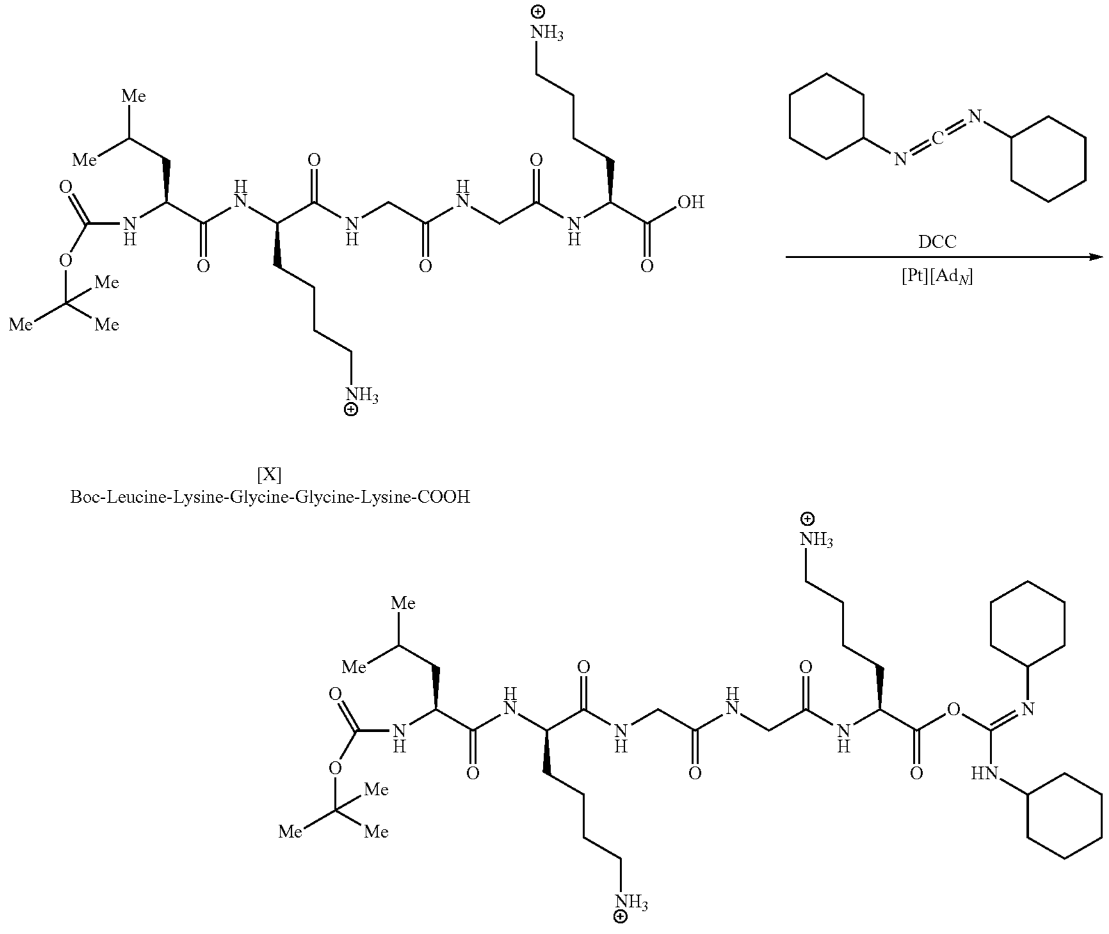
[X]
Boc-Leucine-Lysine-Glycine-Glycine-Lysine-COOH
[XI]
Boc-Leucine-Lysine-Glycine-Glycine-Lysine-DCC
Step A11: Addition of Isoleucine to Boc-Leucine-Lysine-Glycine-Glycine-Lysine-DCC by peptide bond formation.
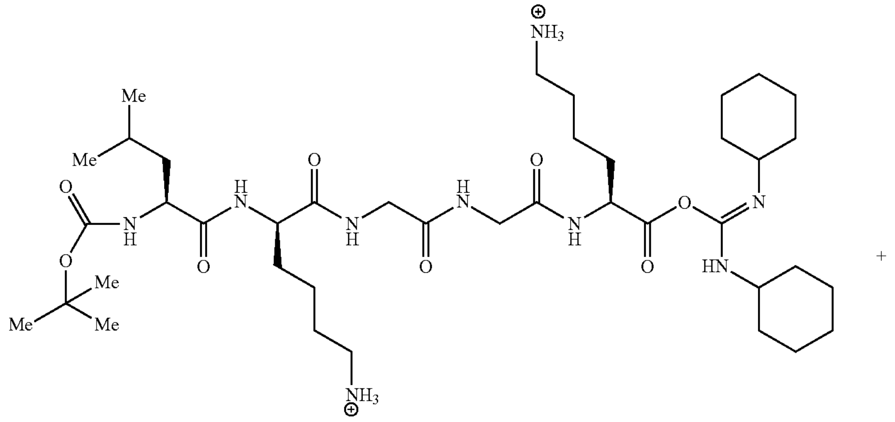
[XI]
Boc-Leucine-Lysine-Glycine-Glycine-Lysine-DCC -continued
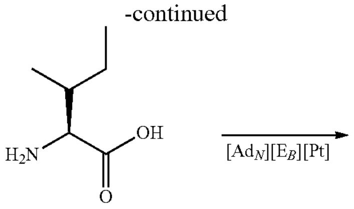
Isoleucine
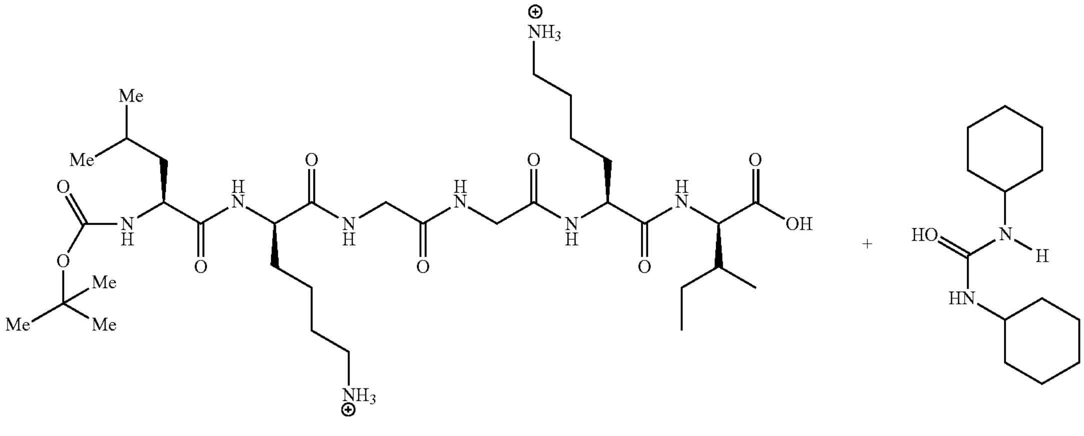
[XII]
Boc-Leucine-Lysine-Glycine-Glycine-Lysine-Isoleucine-COOH
Step A12: Activation of Boc-Leucine-Lysine-Glycine-Glycine-Lysine-Isoleucine with DCC.
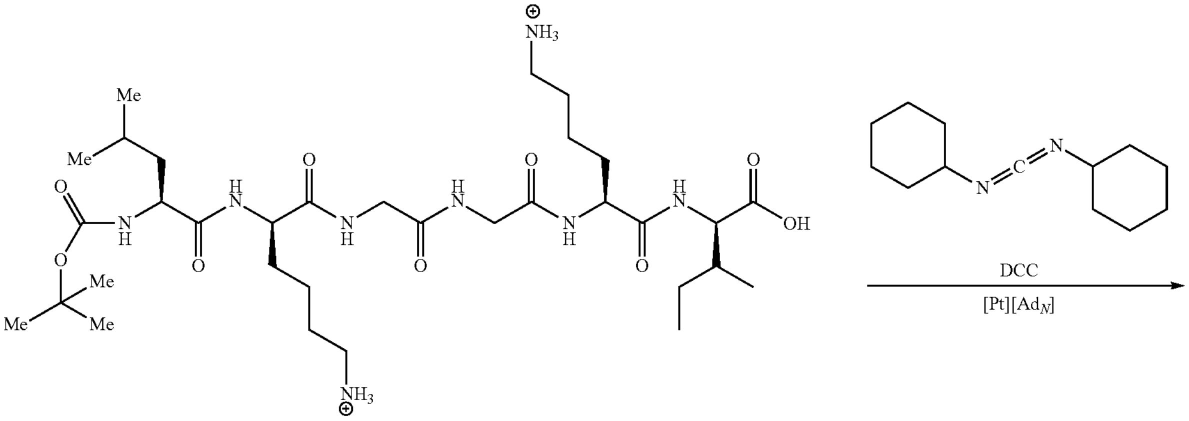
[XII]
Boc-Leucine-Lysine-Glycine-Glycine-Lysine-Isoleucine-COOH -continued
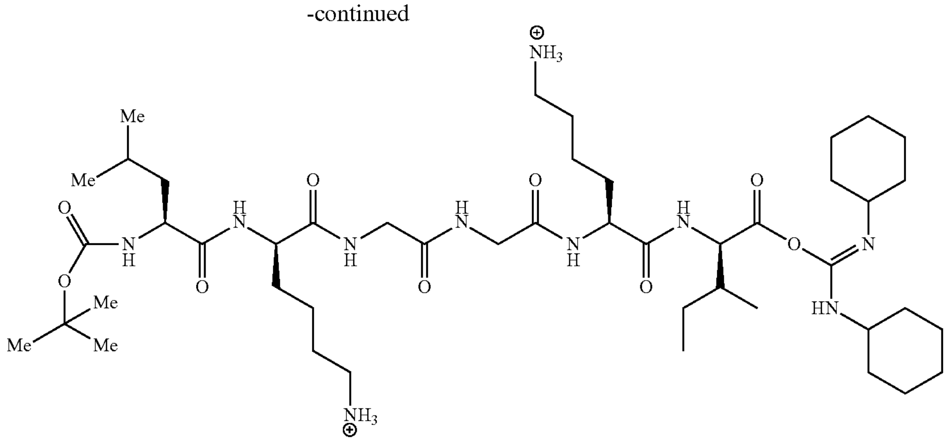
[XIII]
Boc-Leucine-Lysine-Glycine-Glycine-Lysine-Isoleucine-DCC
Step A13: Addition of Valine to Boc-Leucine-Lysine-Glycine-Glycine-Lysine-DCC by peptide bond formation.
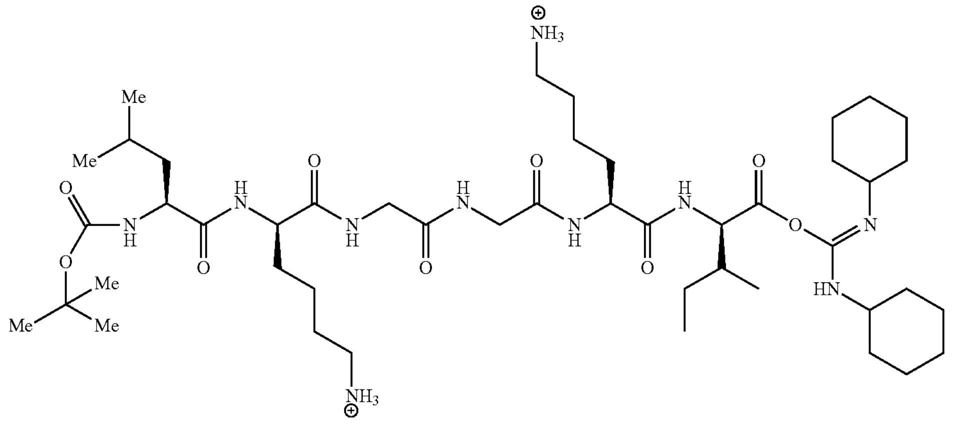
+
[XIII]
Boc-Leucine-Lysine-Glycine-Glycine-Lysine-Isoleucine-DCC
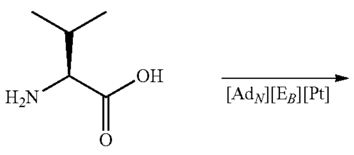
Valine -continued
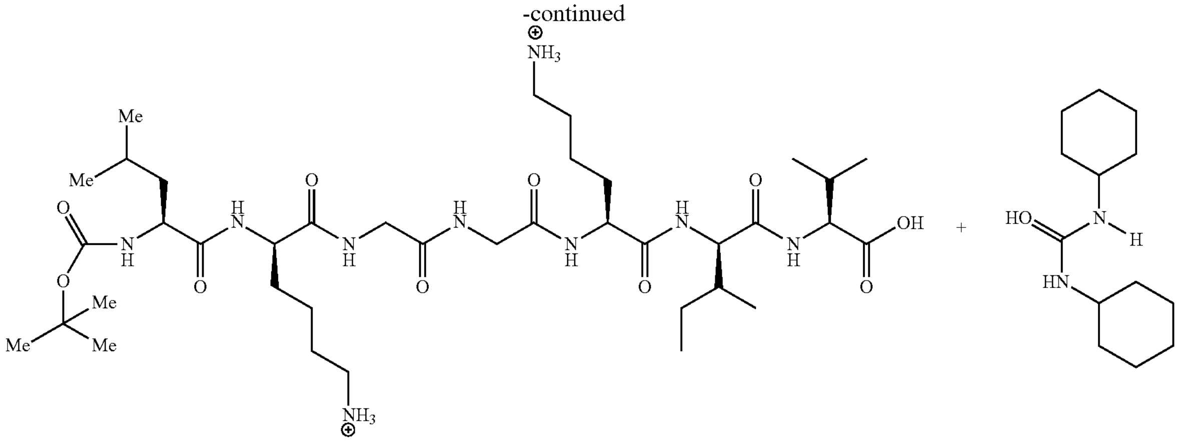
[XIV]
Boc-Leucine-Lysine-Glycine-Glycine-Lysine-Isoleucine-Valine-COOH
Step A14: Reduction of the carbonyl groups using $LiAlH_4$.
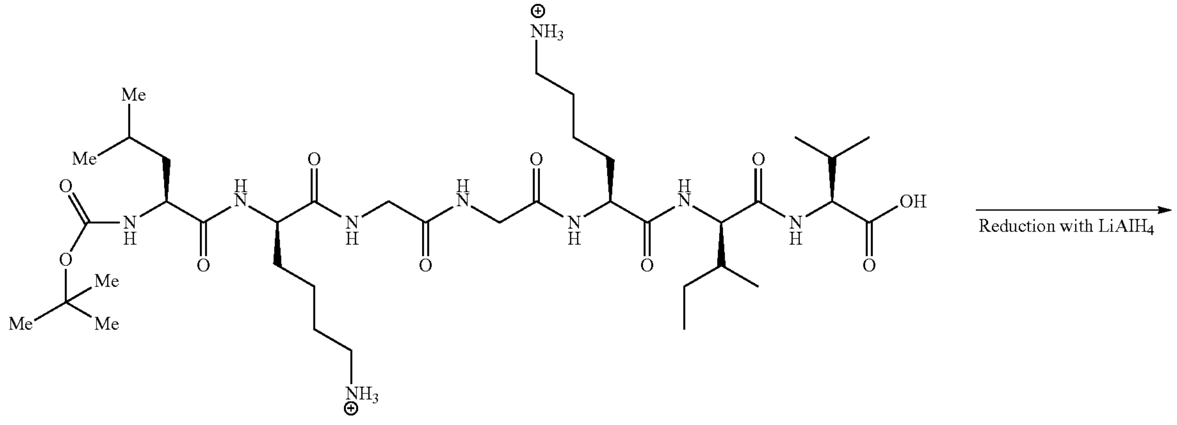
[XIV]
Boc-Leucine-Lysine-Glycine-Glycine-Lysine-Isoleucine-Valine-COOH
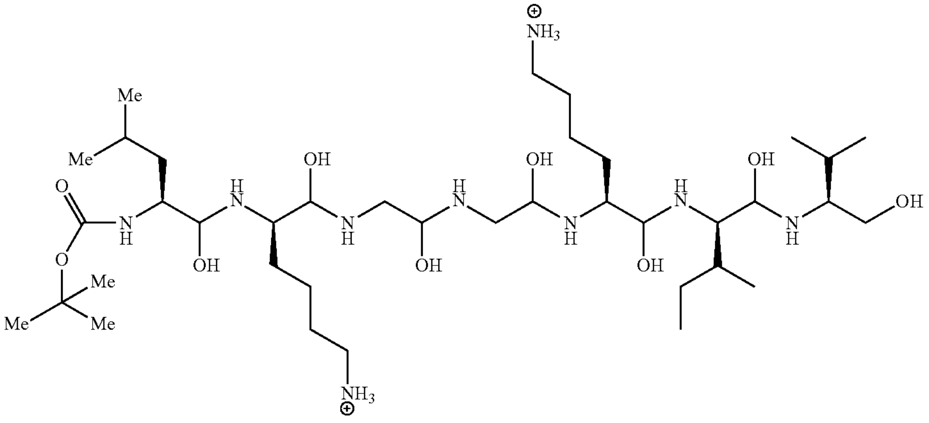
[XV]
Boc-Leucine(RC)-Lysine(RC)-Glycine(RC)-Glycine(RC)-Lysine(RC)-Isoleucine(RC)-Valine-COOH
RC = Reduced Carbonyl Method B: Synthesis of a PLpro Covalent Inhibitor Step B1: Protection of the Amino Group on Arginine with Boc Anhydride (tert-butoxycarbonyl) as in Step A1 above.

Step B2: Activation of the carboxylic acid group on Boc-Arginine with DCC (N,N'-Dicyclohexylcarbodiimide) as in Step A2 above.

Step B3: Addition of Leucine by peptide bond formation as in Step A3 above.

Step B4: Activation of the carboxylic acid group on Boc-Arginine-Leucine with DCC as in Step A4 above.

Step B5: Addition of Arginine to Boc-Arginine-Leucine by peptide bond formation as in Step A5 above.

Step B6: Activation of the carboxylic acid group on Boc-Arginine-Leucine-Arginine with DCC as in Step A6 above.

Step B7: Addition of Glycine to Boc-Arginine-Leucine-Arginine-DCC by peptide bond formation as in Step A7 above.

Step B8: Activation of Boc-Arginine-Leucine-Arginine-Glycine with DCC as in Step A8 above.

Step B9: Addition of Aminoacetaldehyde to Boc-Arginine-Leucine-Arginine-Glycine-DCC by peptide bond formation.

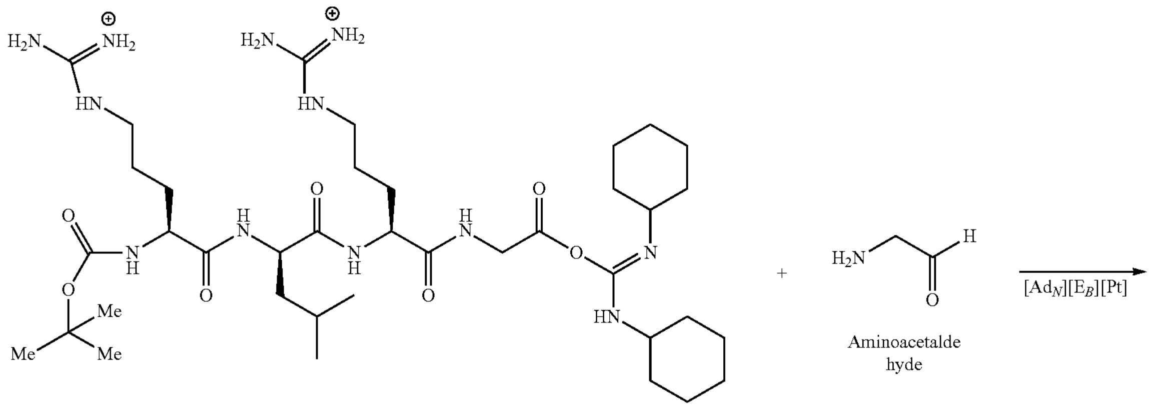

Aminoacetaldehyde

[XVI]
Boc-Arginine-Leucine-Arginine-Glycine-DCC

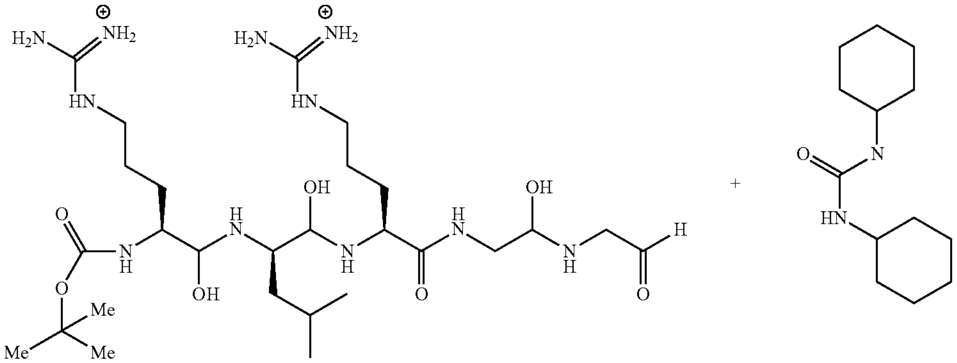

[XVII]
Reduced Boc-Arginine-Leucine-Arginine-Glycine-Aminoacetaldehyde

Step B10: Reduction of the carbonyl groups using $NaBH_4$.

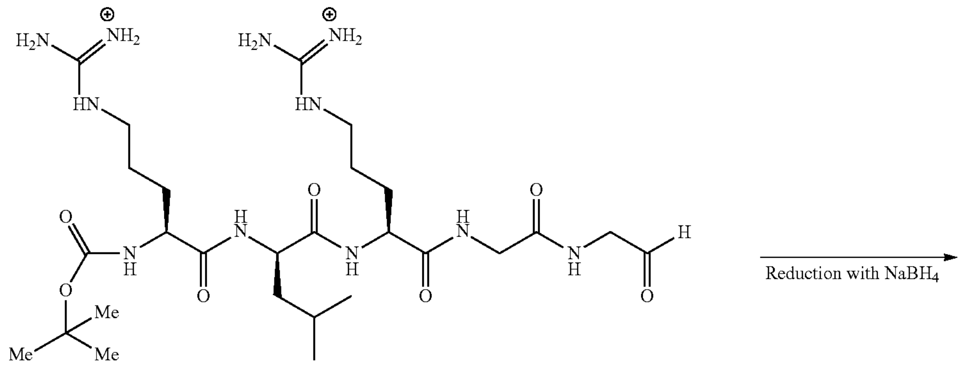

[XVII]
Reduced Boc-Arginine-Leucine-Arginine-Glycine-Aminoacetaldehyde

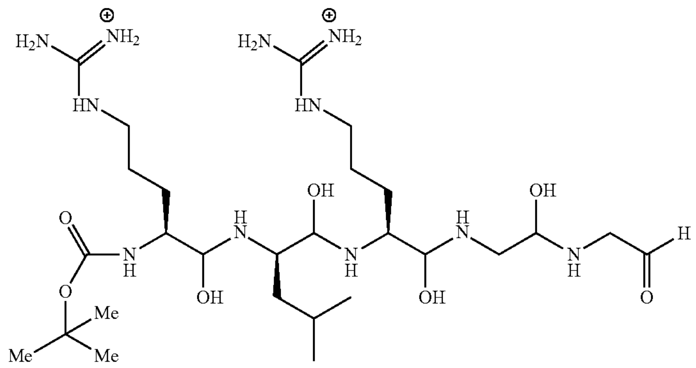

[XVIII]
Reduced Boc-Arginine-Leucine-Arginine-Glycine-Aminoacetaldehyde

Example 4

Assays for Measuring Biological Activity

The effective concentration of a compound of Formula I for use in inhibiting viral protease may be determined through an in vitro titration assays involving enzyme kinetics studies using purified coronavirus PLpro protease and monitoring the levels of enzyme inhibition.

The following peptides were synthesized and tested in vitro in an enzyme inhibition assay.

1)

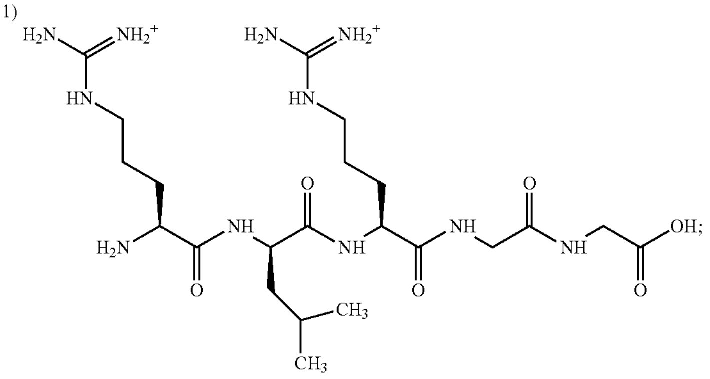

Arg-Leu-Arg-Gly-Gly

-continued

2)

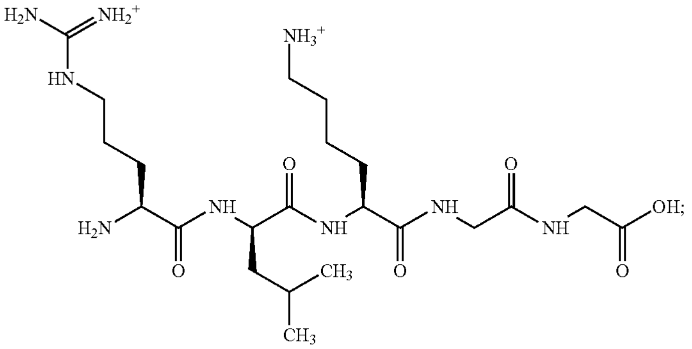

Arg-Leu-Lys-Gly-Gly

3)

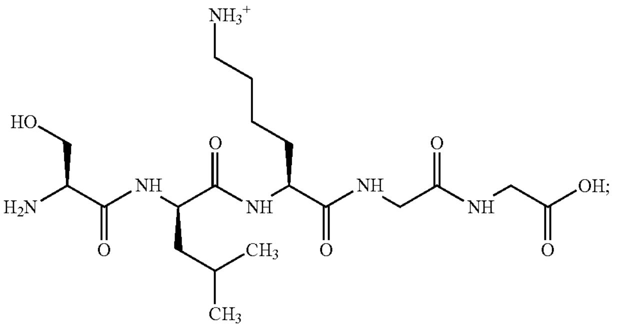

Ser-Leu-Lys-Gly-Gly

4)

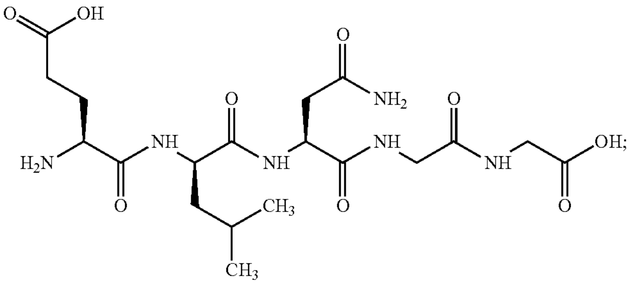

Glu-Leu-Asn-Gly-Gly

5)

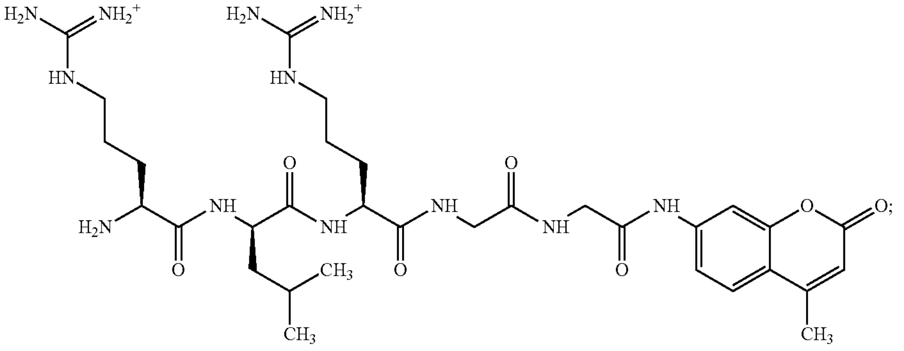

Arg-Leu-Arg-Gly-Gly-AMC

The inhibition assay was carried out as follows. 1 μM SARS-CoV-2-PLpro enzyme was incubated with 25 μM Arg-Leu-Arg-Gly-Gly-AMC substrate and 100 μM of the inhibitor peptide tested, in reaction buffer (100 mM NaCl, 50 mM HEPES [pH=7.5], 0.01 mg/mL bovine serum albumin, and 5 mM DTT) to a final volume of 50 μL. A control reaction with no inhibitory peptide was included and serves as the basis for "no inhibition". Each reaction was carried in triplicate. The percentage inhibition was calculated by dividing the observed enzymatic activity in the presence of an inhibitor by the enzymatic activity when no inhibitor was added. The results were as follows:

TABLE 1

| SARS-CoV-2-PLpro enzyme Inhibition | |
|---|---|
| Peptide | Percent inhibition |
| Arg - Leu - Arg - Gly - Gly | 10-15% |
| Arg - Leu - Lys - Gly - Gly | 5-10% |
| Ser - Leu - Lys - Gly - Gly | 0% |
| Glu - Leu - Asn - Gly - Gly | 0% |

Additional in vitro studies could involve determination of the levels of viral replication using mammalian cells infected with coronavirus. The lowest concentration that provides maximal inhibition of protease activity or viral replication in the absence of cellular toxicity will be dependent on the compound's intrinsic potency and its ability to inhibit coronavirus protease. This optimal concentration is then used to treat mice or rats infected with coronavirus to further determine inhibition activity levels and appropriate in vivo concentrations. Useful concentrations range from 1 nM to 1 mM in aqueous buffer or cell media. Preferably, the concentration used is between 0.01 μM and 100 μM.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A compound of formula II, or a pharmaceutically acceptable salts thereof, and stereoisomers thereof:

(II)

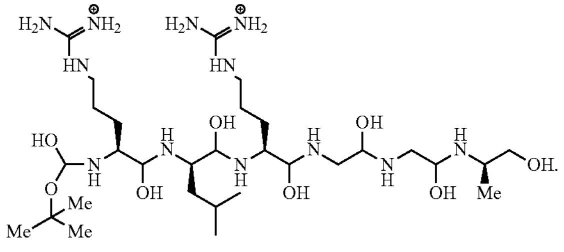

2. A pharmaceutical composition comprising the compound of claim 1, or a pharmaceutically acceptable salt thereof, and a pharmaceutically acceptable carrier.

* * * * *